(12) United States Patent
Paul et al.

(10) Patent No.: US 7,621,956 B2
(45) Date of Patent: Nov. 24, 2009

(54) PROSTHETIC SPINAL DISC REPLACEMENT

(75) Inventors: David C. Paul, Phoenixville, PA (US); Christopher Angelucci, Schwenksville, PA (US)

(73) Assignee: Globus Medical, Inc., Audubon, PA (US)

( * ) Notice: Subject to any disclaimer, the term of this patent is extended or adjusted under 35 U.S.C. 154(b) by 248 days.

(21) Appl. No.: 10/827,642

(22) Filed: Apr. 20, 2004

(65) Prior Publication Data

US 2005/0043800 A1    Feb. 24, 2005

Related U.S. Application Data

(60) Provisional application No. 60/491,271, filed on Jul. 31, 2003.

(51) Int. Cl.
*A61F 2/44*    (2006.01)
(52) U.S. Cl. .................................................. 623/17.15
(58) Field of Classification Search ............... 606/61; 623/17.11, 17.14, 17.15, 17.16
See application file for complete search history.

(56) References Cited

U.S. PATENT DOCUMENTS

| | | | | |
|---|---|---|---|---|
| 4,349,921 A | * | 9/1982 | Kuntz | ....................... 623/17.16 |
| 4,759,766 A | | 7/1988 | Buettner-Janz et al. | |
| 4,997,432 A | | 3/1991 | Keller | |
| 5,122,130 A | | 6/1992 | Keller | |
| 5,246,458 A | | 9/1993 | Graham | |
| 5,258,031 A | | 11/1993 | Salib et al. | |
| 5,314,477 A | | 5/1994 | Marnay | |
| 5,401,269 A | | 3/1995 | Buettner-Janz et al. | |
| 5,425,773 A | * | 6/1995 | Boyd et al. | ............... 623/17.15 |
| 5,507,816 A | | 4/1996 | Bullivant | |
| 5,534,029 A | | 7/1996 | Shima | |
| 5,556,431 A | | 9/1996 | Buettner-Janz | |
| 5,562,738 A | | 10/1996 | Boyd et al. | |
| 5,676,701 A | * | 10/1997 | Yuan et al. | ............... 623/17.15 |
| 5,683,465 A | | 11/1997 | Shinn et al. | |
| 5,702,450 A | * | 12/1997 | Bisserie | ................... 623/17.16 |
| 5,755,796 A | | 5/1998 | Ibo | |
| 5,888,226 A | | 3/1999 | Rogozinski | |
| 5,895,428 A | | 4/1999 | Berry | |
| 5,899,941 A | | 5/1999 | Nishijima et al. | |

(Continued)

FOREIGN PATENT DOCUMENTS

EP        0955021        3/1998

(Continued)

OTHER PUBLICATIONS

ISR -PCT/US04/24933, Oct. 27, 2006, Paul.

(Continued)

*Primary Examiner*—Thomas C Barrett
*Assistant Examiner*—Nicholas Woodall

(57) ABSTRACT

The present invention relates generally to a prosthetic spinal disc for replacing a damaged disc between two vertebrae of a spine. The present invention also relates to a method for implanting a prosthetic spinal disc via posterior or posterior lateral implantation. Other surgical approaches for implanting the prosthetic disc may also be used. The present invention also involves a method for implanting the prosthetic spinal disc while either avoiding or minimizing contact with the spinal cord and nerve rootlets, or reducing the time and extent that they need to be repositioned during implantation.

49 Claims, 25 Drawing Sheets

U.S. PATENT DOCUMENTS

| | | | |
|---|---|---|---|
| 6,039,763 A | 3/2000 | Shelokov | |
| 6,063,121 A | 5/2000 | Xavier et al. | |
| 6,080,157 A | 6/2000 | Cathro et al. | |
| 6,113,637 A | 9/2000 | Gill et al. | |
| 6,146,421 A | 11/2000 | Gordon | |
| 6,146,422 A | 11/2000 | Lawson | |
| 6,156,067 A | 12/2000 | Bryan et al. | |
| 6,179,874 B1 * | 1/2001 | Cauthen | 623/17.14 |
| 6,228,118 B1 | 5/2001 | Gordon | |
| 6,368,350 B1 | 4/2002 | Erickson et al. | |
| 6,375,682 B1 | 4/2002 | Fleischmann et al. | |
| 6,416,551 B1 | 7/2002 | Keller | |
| 6,468,310 B1 | 10/2002 | Ralph et al. | |
| 6,540,785 B1 | 4/2003 | Gill et al. | |
| 6,635,087 B2 | 10/2003 | Angelucci et al. | |
| 6,660,007 B2 | 12/2003 | Khanna | |
| 6,682,562 B2 | 1/2004 | Viart et al. | |
| 6,706,068 B2 | 3/2004 | Ferree | |
| 6,712,852 B1 | 3/2004 | Chung et al. | |
| 6,890,355 B2 * | 5/2005 | Michelson | 623/17.11 |
| 6,997,953 B2 | 2/2006 | Chung et al. | |
| 7,083,649 B2 * | 8/2006 | Zucherman et al. | 623/17.11 |
| 2002/0035400 A1 * | 3/2002 | Bryan et al. | 623/17.15 |
| 2002/0111681 A1 | 8/2002 | Ralph et al. | |
| 2002/0111682 A1 | 8/2002 | Ralph et al. | |
| 2002/0111683 A1 | 8/2002 | Ralph et al. | |
| 2002/0111684 A1 | 8/2002 | Ralph et al. | |
| 2002/0111685 A1 | 8/2002 | Ralph et al. | |
| 2002/0111686 A1 | 8/2002 | Ralph et al. | |
| 2002/0111687 A1 | 8/2002 | Ralph et al. | |
| 2002/0120335 A1 | 8/2002 | Angelucci et al. | |
| 2003/0045935 A1 | 3/2003 | Angelucci et al. | |
| 2003/0045936 A1 | 3/2003 | Angelucci et al. | |
| 2003/0125738 A1 | 7/2003 | Khanna | |
| 2003/0125740 A1 | 7/2003 | Khanna | |
| 2003/0204261 A1 * | 10/2003 | Eisermann et al. | 623/17.14 |
| 2003/0233094 A1 | 12/2003 | Squires | |
| 2004/0030388 A1 | 2/2004 | Null et al. | |
| 2004/0064184 A1 | 4/2004 | Chung et al. | |
| 2004/0117022 A1 * | 6/2004 | Marnay et al. | 623/17.16 |
| 2004/0138750 A1 * | 7/2004 | Mitchell | 623/17.11 |
| 2004/0143332 A1 | 7/2004 | Krueger | |
| 2004/0153155 A1 | 8/2004 | Chung et al. | |
| 2004/0153157 A1 | 8/2004 | Keller | |
| 2004/0172135 A1 * | 9/2004 | Mitchell | 623/17.15 |
| 2004/0210222 A1 | 10/2004 | Angelucci et al. | |
| 2004/0215198 A1 | 10/2004 | Marnay | |
| 2004/0220582 A1 | 11/2004 | Keller | |
| 2004/0225365 A1 * | 11/2004 | Eisermann et al. | 623/17.15 |
| 2004/0243240 A1 | 12/2004 | Beaurain | |
| 2005/0021145 A1 * | 1/2005 | de Villiers et al. | 623/17.14 |
| 2005/0038511 A1 | 2/2005 | Martz | |
| 2005/0107877 A1 | 5/2005 | Blain | |
| 2005/0131412 A1 | 6/2005 | Olevsky et al. | |
| 2005/0251138 A1 | 11/2005 | Boris et al. | |
| 2005/0261773 A1 * | 11/2005 | Ferree | 623/17.16 |
| 2005/0273100 A1 | 12/2005 | Taylor | |
| 2006/0036325 A1 | 2/2006 | Paul et al. | |
| 2006/0116768 A1 * | 6/2006 | Krueger et al. | 623/17.14 |
| 2007/0010826 A1 | 1/2007 | Rhoda et al. | |
| 2007/0055378 A1 | 3/2007 | Ankney et al. | |

FOREIGN PATENT DOCUMENTS

| | | |
|---|---|---|
| WO | WO 99/05995 | 2/1999 |
| WO | WO 00/23015 | 4/2000 |
| WO | WO 00/42944 | 7/2000 |

OTHER PUBLICATIONS

IPRP-PCT/US04/24933, Dec. 8, 2006, Paul.

* cited by examiner

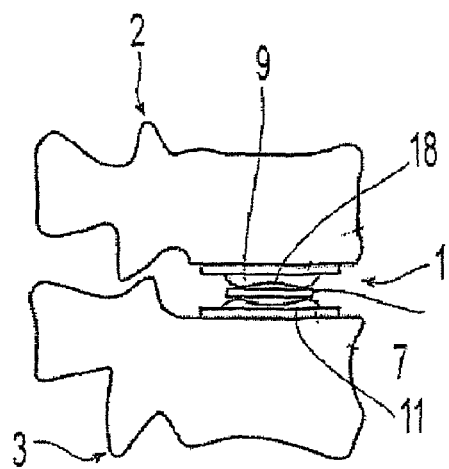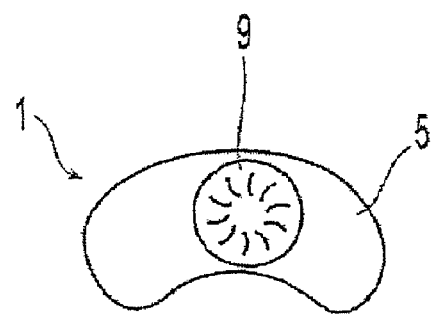
Fig. 1A      Fig. 1B
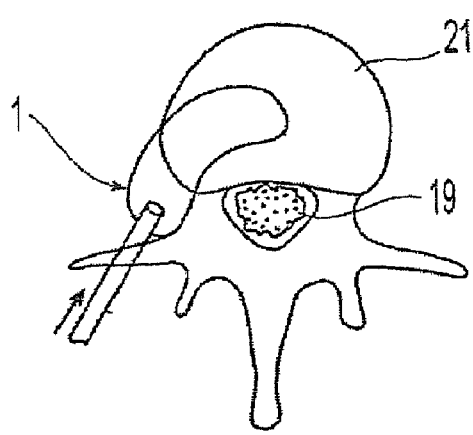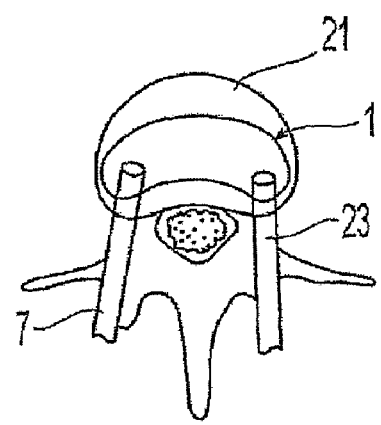
Fig. 2A      Fig. 2B
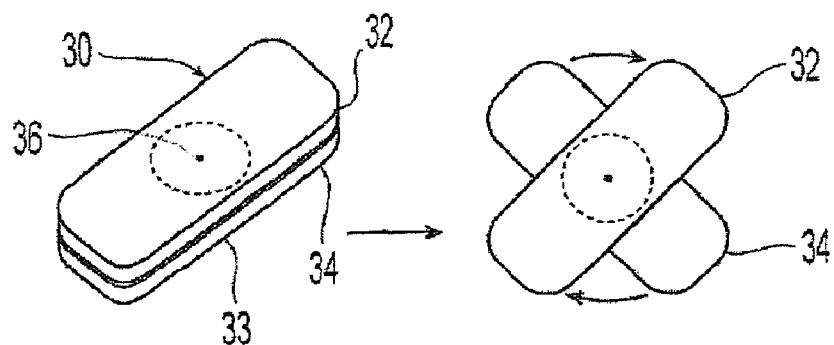
Fig. 3

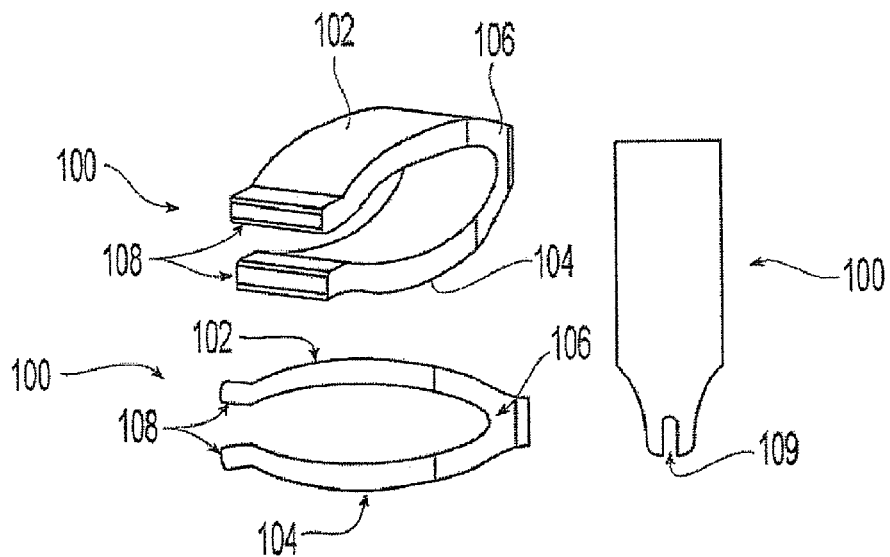
*Fig. 7A*
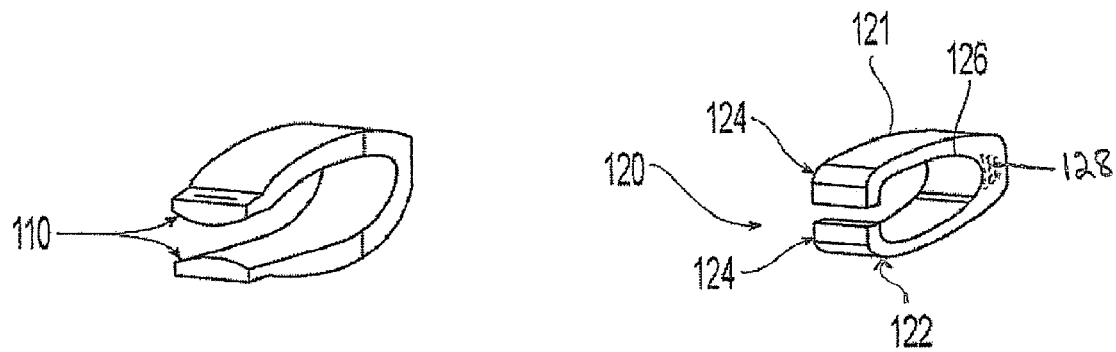
*Fig. 7B*  *Fig. 8A*
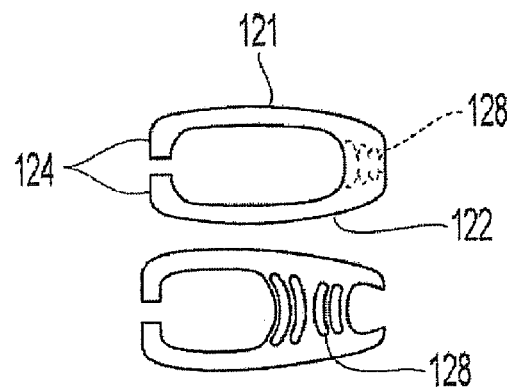
*Fig. 8B*

*Fig. 12*
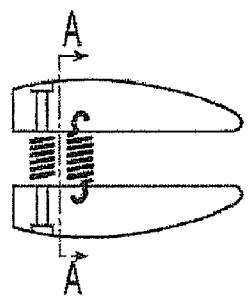 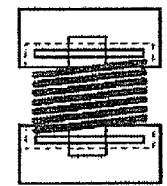
*Fig. 13*  *Fig. 14*
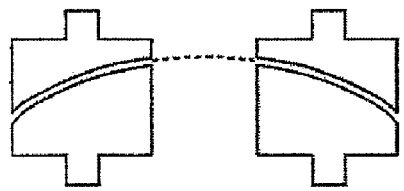 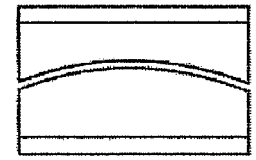
*Fig. 15*  *Fig. 16*
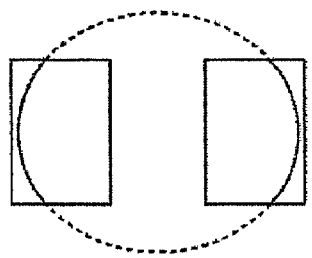 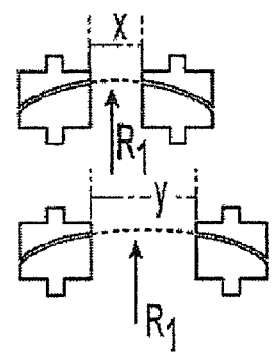
*Fig. 17*  *Fig. 18*

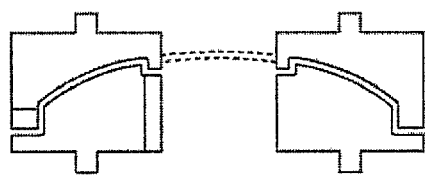
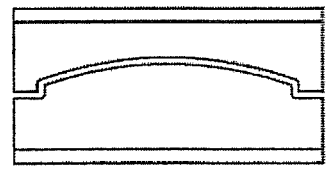
*Fig. 19*   *Fig. 20*
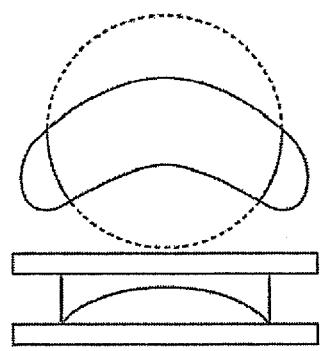
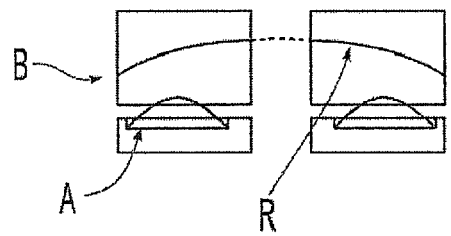
*Fig. 21*   *Fig. 22*
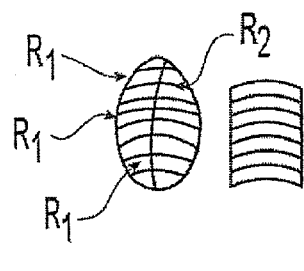
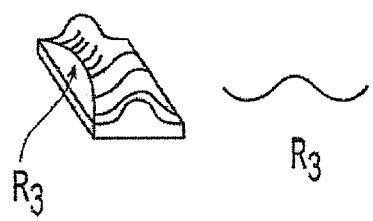
*Fig. 23*   *Fig. 24*

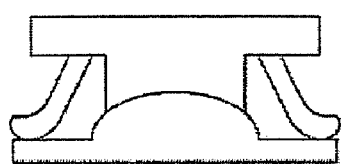
Fig. 33
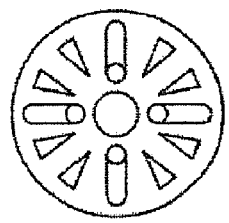
Fig. 34
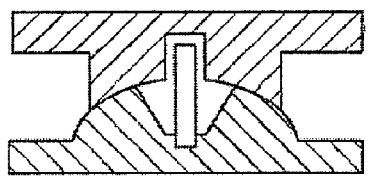
Fig. 35
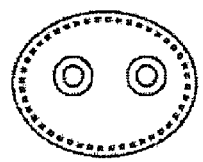 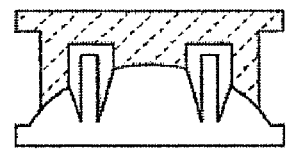
Fig. 37
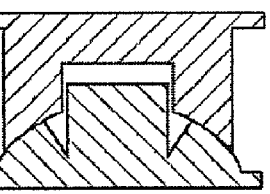
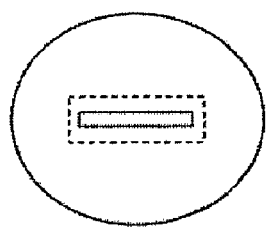
Fig. 36
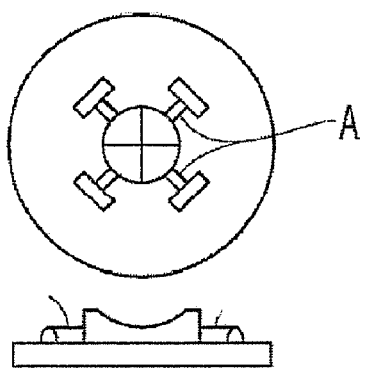
Fig. 38
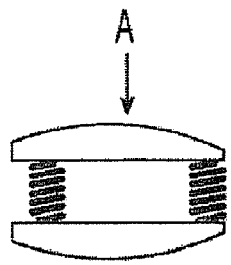
Fig. 39

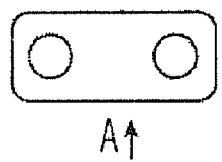 
Fig. 40　　　　　　　　　Fig. 41
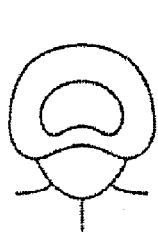 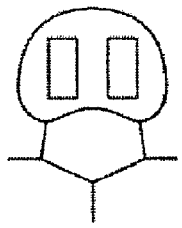 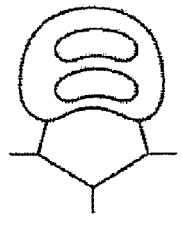 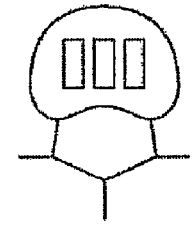
Fig. 42A　Fig. 42B　Fig. 42C　Fig. 42D
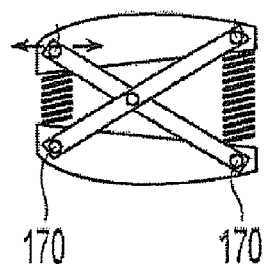 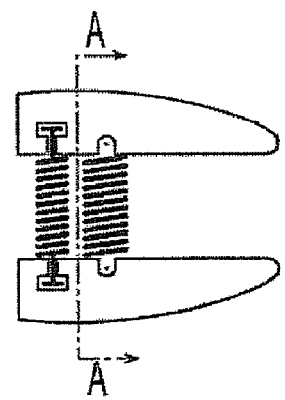
Fig. 43　　　　　　　　　Fig. 44

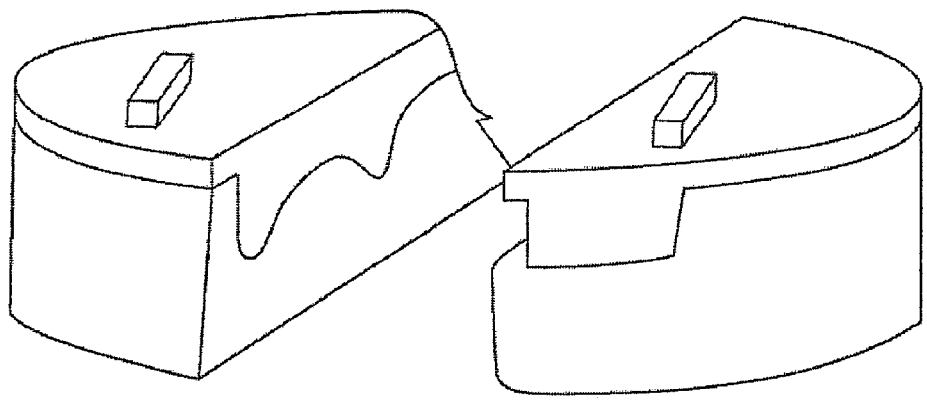
Fig. 54
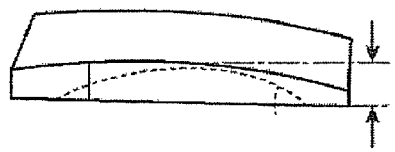 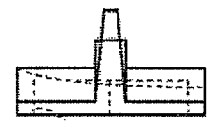
Fig. 55  Fig. 56
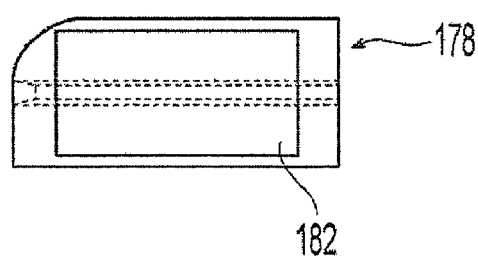

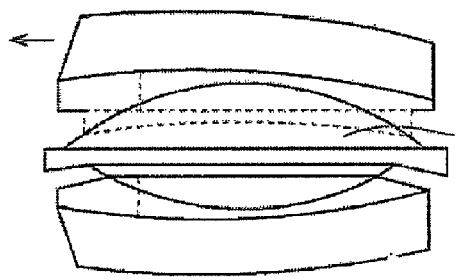
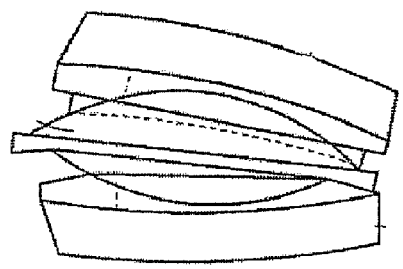
Fig. 59                    Fig. 60
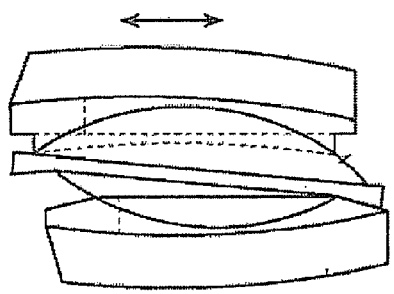
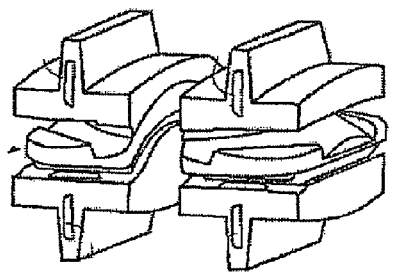
Fig. 61                    Fig. 62A
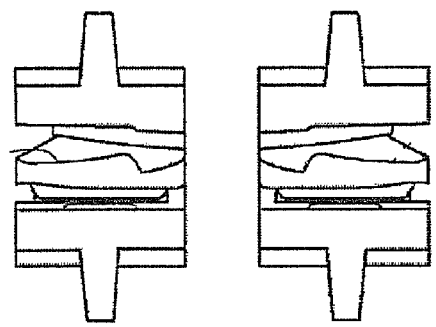
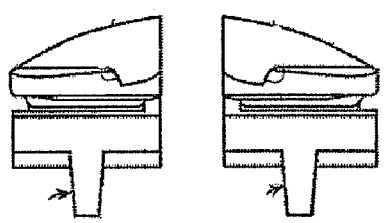
Fig. 62B                   Fig. 62C

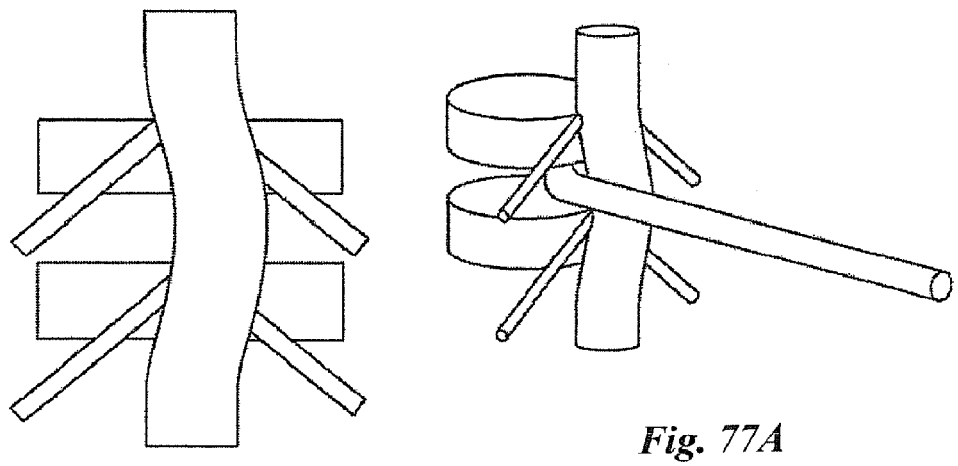
Fig. 76
Fig. 77A
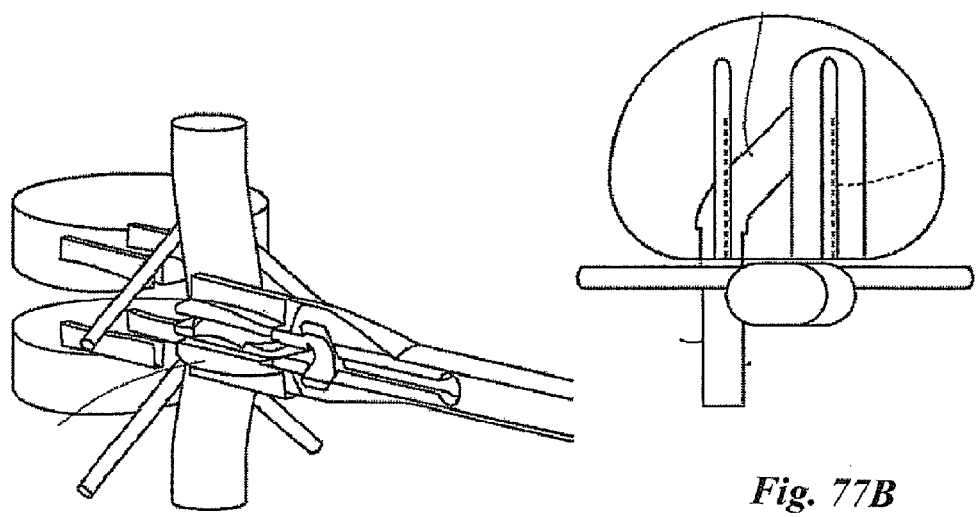
Fig. 78
Fig. 77B

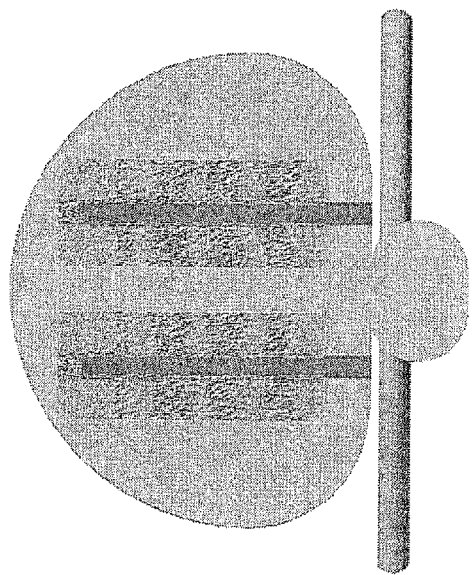
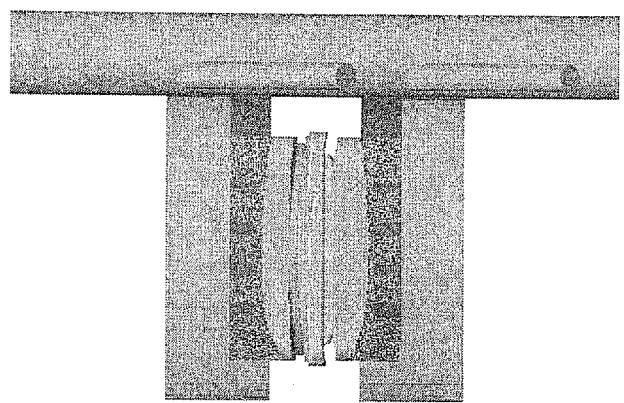
Fig. 79

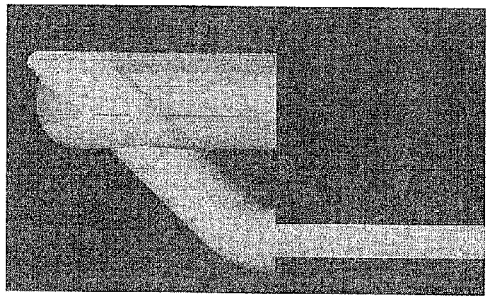
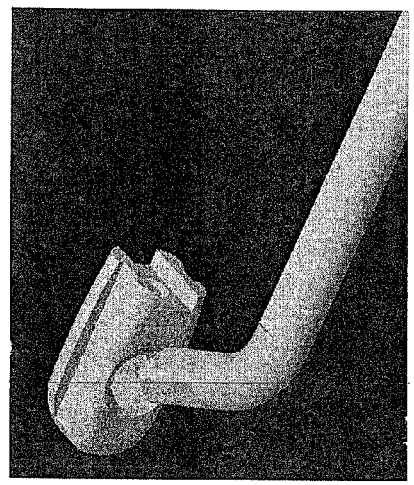
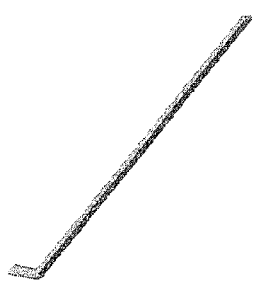
Fig. 82

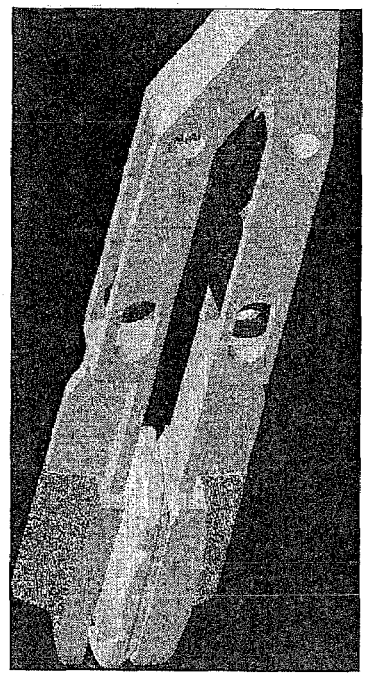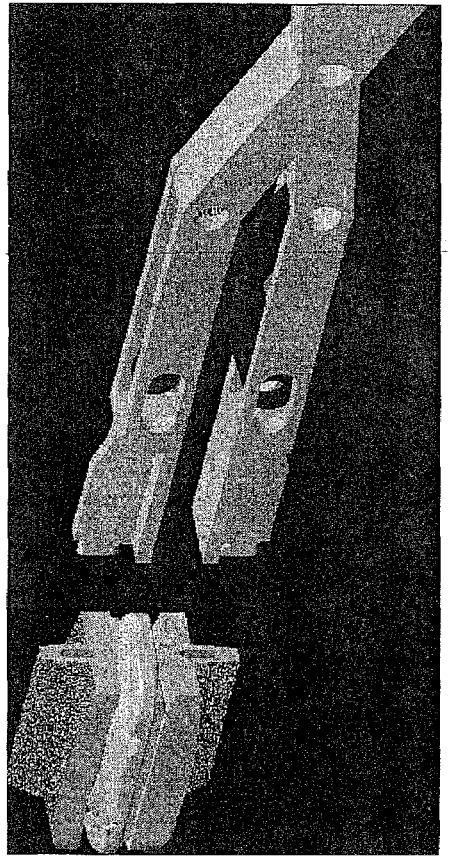
Fig. 83

PROSTHETIC SPINAL DISC REPLACEMENT

CROSS REFERENCE TO RELATED APPLICATIONS

This application claims priority to provisional application serial No. 60/491,271 filed on Jul. 31, 2003 and entitled "Posterior Prosthtetic Spinal Disc", the entirety of which is incorporated herein by reference thereto.

FIELD OF THE INVENTION

The present invention relates to a prosthetic spinal disc for fully or partially replacing a damaged disc between two vertebrae of a spine. The present invention also relates to a method for implanting a prosthetic spinal disc via posterior or posterior lateral implantation, although other implantation approaches may also be used.

BACKGROUND OF THE INVENTION

The vertebrate spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral forming of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the anulus fibrosus ("anulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The anulus of the disc is a tough, outer fibrous ring which binds together adjacent vertebrae. The fibrous portion, which is much like a laminated automobile tire, measures about 10 to 15 millimeters in height and about 15 to 20 millimeters in thickness. The fibers of the anulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the anulus is the nucleus. The healthy nucleus is largely a gel-like substance having high water content, and like air in a tire, serves to keep the anulus tight yet flexible. The nucleus-gel moves slightly within the anulus when force is exerted on the adjacent vertebrae while bending, lifting, and other motions.

The spinal disc may be displaced or damaged due to trauma, disease, degenerative defects, or wear over an extended period of time. A disc herniation occurs when the anulus fibers are weakened or torn and the inner tissue of the nucleus becomes permanently bulged, distended, or extruded out of its normal, internal anulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the anulus to buckle in areas where the laminated plies are loosely bonded. As these overlapping laminated plies of the anulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all discal motion is lost in the fused segment. Ultimately this procedure places a greater stress on the discs adjacent to the fused segment as they compensate for lack of motion, perhaps leading to premature degeneration of those adjacent discs.

As an alternative to vertebral fusion, various prosthetic discs have been developed. The first prosthetics embody a wide variety of ideas, such as ball bearings, springs, metal spikes and other perceived aids. These prosthetics are all made to replace the entire intervertebral disc space and are large and rigid. Beyond the questionable applicability of the devices is the inherent difficulties encountered during implantation. Due to their size and inflexibility, these devices require an anterior implantation approach as the barriers presented by the lamina and, more importantly, the spinal cord and nerve rootlets during posterior or posterior lateral implantation is difficult to avoid.

Anterior implantation, however, can involve numerous risks during surgery. Various organs present physical obstacles as the surgeon attempts to access the damaged disc area from the front of the patient. After an incision into the patient's abdomen, the surgeon is forced to navigate around interfering organs and carefully move them aside in order to gain access to the spine. One risk to the patient from an anterior approach is that these organs may be inadvertently damaged during the procedure.

In contrast, a posterior approach to intervertebral disc implantation avoids the risks of damaging body organs. Despite this advantage, a posterior approach also raises other difficulties that have discouraged it use. For instance, a posterior approach can introduce a risk of damaging the spinal cord. Additionally, vertebral body geometry allows only limited access to the intervertebral discs. Thus, the key to successful posterior or posterior lateral implantation is avoiding contact with the spinal cord, as well as being able to place an implant through a limited special area due to the shape of the vertebral bones. Because an anterior approach does not present the space limitations that occur with a posterior approach, current prosthetic disc designs are too bulky to safely use with a posterior approach. Therefore, a substantial need exists for a method of surgically implanting a prosthetic spinal disc into the intervertebral disc space through a posterior approach with minimal contact with the spinal cord.

SUMMARY OF THE INVENTION

In general, the present invention is directed toward prosthetic disc designs. One embodiment of the invention has an intervertebral artificial disc for replacement of a damaged spinal disc between two vertebrae. The artificial disc has facing endplates made of rigid material. One plate of rigid material has a surface that can engage with an endplate of a vertebral body. The rigid plate may have a contoured, partially spherical seating surface. A second rigid plate having a second surface engages with the endplate of a second vertebral body, and has a contoured, partially cylindrical seating surface. A core element may be at least partially disposed between the first and second rigid plates. Moreover, the core element may have contoured surfaces in communication with and substantially corresponding to the curvature of the first and second rigid plate seating surfaces.

In one embodiment, one or both of the rigid plates are configured to correspond to the natural curvature and shape of the vertebral body endplates. In another embodiment, however, one or both of the rigid plates are configured to correspond to a predetermined cut shape or contour. Thus, the surface of the vertebral body that contacts the rigid plate may be shaped or prepared for receiving a portion of the prosthetic disc. In one example embodiment, the portion of one or both plates that contacts a vertebral body is substantially flat.

In another embodiment, the prosthetic disc is formed from a plurality of assemblies. The first assembly comprises the first rigid plate, second rigid plate, and core element. The second assembly comprises a third rigid plate configured and adapted to engage with the first endplate of the first vertebral body, and has a contoured, partially spherical seating surface having substantially the same radius of curvature as the first rigid plate seating surface. The second assembly also may have a fourth rigid plate configured and adapted to engage with the second endplate of the second vertebral body, and having a contoured, partially cylindrical seating surface having substantially the same radius of curvature as the second rigid plate seating surface. Likewise, the second assembly may have a second core element at least partially disposed between the third and fourth rigid plates, wherein the second core element has a contoured surfaces substantially corresponding to the curvature of the third and fourth rigid plate seating surfaces.

In another embodiment, one seating surface of the plates may permit rotation of the core element relative to the second rigid plate substantially in the sagittal plane. In another embodiment, the second rigid plate may have a longitudinal axis and wherein the axis of rotation of the core element forms an angle from about 20° to about 70°. In yet another embodiment, the second rigid plate has a longitudinal axis and the axis of rotation of the core element is substantially perpendicular to the longitudinal axis. In one embodiment, the axis of rotation of the core element is substantially parallel to the longitudinal axis of the second rigid plate.

The longitudinal axis of one or more rigid plates and the axis of rotation of the core element need not be aligned in the same direction. For example, in one embodiment, the angle between the second rigid plate longitudinal axis and the core element axis of rotation permitted by the seating surface of the second plate forms an angle from about 30° to about 60°.

Several embodiments of the present invention are directed toward an artificial disc that is capable of providing a moving IAR. In one embodiment, the moving IAR achieved is substantially in the sagittal plane.

In many embodiments, the contact between the first rigid plate seating surface and the first contoured surface of the first core element extends over an area. Likewise, the the second rigid plate seating surface and the second contoured surface of the first core element may also extend over an area. While it is preferred that both the first and second seating surfaces contact the core element over an area, one or both surfaces may be configured to contact the core element along a line or a point. For instance, in one embodiment the contact between the second rigid plate seating surface and the second contoured surface of the first core element forms a line of contact.

In some embodiments, the orientation or relative position of the seating surfaces may be specified. For example, in one embodiment the first rigid plate is disposed above the first core element and the second rigid plate is disposed below the first core element.

In another embodiment, one or both rigid plates may have a keel or raised ridge of material that extends at least partially into the endplate of the vertebral body that they contact. A variety of materials may be used to form the components of the invention. For instance, in one embodiment the first core element is at least partially formed of an elastomeric material.

The artificial disc may also have mechanical stops that limit movement of the disc. For example, stops may be provided to prevent lateral bending greater than 10 degrees in each direction. In addition, mechanical stops may prevent total axial rotation greater than 5 to 10 degrees.

The curvature of the seating surfaces may be convex or concave. In one embodiment, the curvature of the second rigid plate seating surface is convex. In another embodiment, the curvature of the second rigid plate seating surface is concave. The dimensions of each component also may be varied. For example, in one embodiment the first rigid plate may have a length from about 18 to about 35 mm, while in another embodiment the first rigid plate may have a length from about 22 to about 26 mm. In yet another embodiment, the first rigid plate may have a width from about 9 mm to about 18 mm, or alternatively may be from about 7 mm to about 15 mm. In still another embodiment, the first rigid plate has a width from about 8 to about 12 mm, and in a further embodiment the first rigid plate has a width from about 12 mm to about 36 mm. Moreover, other embodiments the first rigid plate may have a width from about 16 mm to about 28 mm, or from about 12 to abut 14 mm.

In one embodiment the core element and first rigid plate are formed from substantially similar materials, while in another embodiment the core element is formed from a different material that the first rigid plate. In one embodiment, the core comprises a high molecular weight polymeric material, and more specifically may comprise a high molecular weight polyethylene. The core may also be formed from polyetherketone (PEEK) or other radio translucent materials. In embodiments where radio translucent materials are used, the core may have a radio opaque marker that is capable of indicating the orientation of the core. For example, the radio opaque marker may be two or more metallic pins with orientations that permit identification of the orientation of the core.

Methods for replacing a damaged spinal disc between two vertebrae are also contemplated by the present invention. One embodiment involves the steps of removing a damaged spinal disc disposed between two vertebral bodies, providing and positioning a first artificial disc assembly therebetween. In some instances, one or both endplates of the vertebral bodies may be prepared for receiving the artificial disc. More than one disc assembly may also be used to form the artificial disc.

BRIEF DESCRIPTION OF THE DRAWINGS

FIG. 1 is a side view of sequentially aligned vertebral bodies, such as are found in the cervical, thoracic and lumbar spine, and a posterior prosthetic spinal disc located between the vertebral bodies.

FIG. 2 is a posterior view of sequentially aligned vertebral bodies and a posterior prosthetic spinal disc located between the vertebral bodies.

FIG. 3 is a view of a collapsed posterior prosthetic spinal disc that can be opened via scissor action.

FIGS. 7A and 7B show C-shaped discs having a flexible portion, curved end plates and stops.

FIGS. 8A and 8B show a C-shaped disc having slots that create flexibility.

FIGS. 12-14 illustrate the use of compressed elements in the present invention.

FIGS. 15-26 illustrate the use of varying types interfacing surfaces in the present invention to achieve or restrict movement in different directions.

FIGS. 30-45 illustrate the use of several stiffness mechanisms that may be used in the present invention.

FIGS. 51-54 show a second example of the present invention having a fixed IAR.

FIGS. 55-61 show a third example of the present invention with two articulating surfaces.

FIGS. 68-83 illustrate further approaches and instruments according of the present invention.

DETAILED DESCRIPTION OF THE INVENTION

Figure 4:
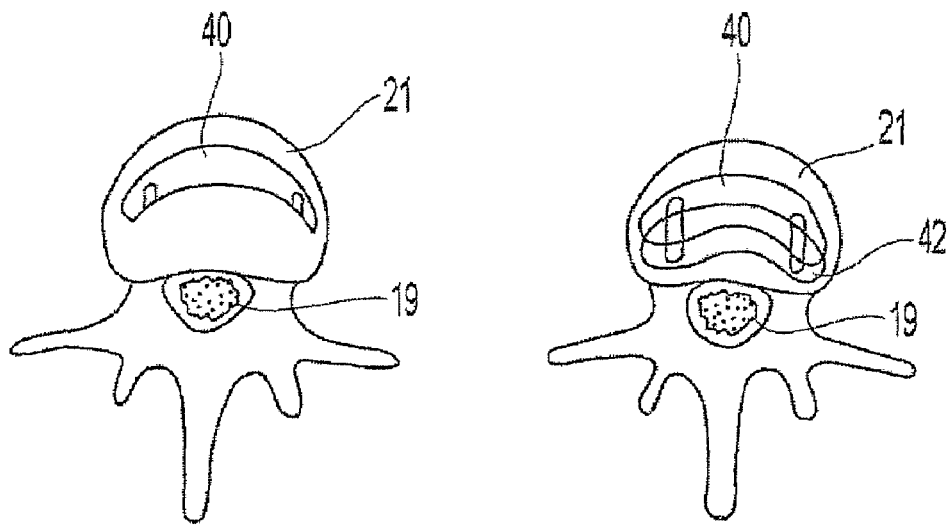
FIG. 4 is a top view of segmented posterior prosthetic spinal discs and their assembly between vertebral bodies.

The present invention relates generally to a posterior prosthetic spinal disc for replacing a damaged disc between two vertebrae of a spine. The present invention also relates to a method for implanting a prosthetic spinal disc via posterior or posterior lateral implantation. In particular, the present invention encompasses a method for implanting the prosthetic spinal disc while avoiding or minimizing contact with the spinal cord.

As described in greater detail below, the prosthetic spinal disc may be articulating or non-articulating. In addition, the prosthetic disc may be formed of one, two, three or more units. For example, two units may be disposed in the medial-lateral direction at spaced apart locations, and the upper and lower portions of each unit have interfacing surfaces that form an arc in the anterior-posterior direction.

If multiple units are used, they may be spaced apart from each other or connected to prior to insertion in the patient or as they are being positioned within the body. The ability to connect the units together may allow the prosthetic disc to be inserted using a posterior approach with less risk of injuring the spinal cord, nerve rootlets, lamina or the like. In addition, using a plurality of units, either connected or disposed in spaced apart locations, allows individual units to be interchangeable with a multiplicity of designs or configurations that allow the physician to address different physical conditions of the treated area of the spine and to custom tailor the range of motion that the prosthetic disc will permit.

Several embodiments of the invention illustrate different examples of how the interfacing surfaces of an articulating prosthetic disc may be formed. For instance, articulation may be accomplished with one interfacing surface, such as a ball and joint (see e.g., FIG. 21), or alternatively may be accomplished with two or more interfacing surfaces such as a core disposed between an upper and lower seating surface (see, e.g., FIG. 1A). The configuration of the surface contact may vary to permit or restrict different types and ranges of motion of the treated area. Thus, the contact profile of the interfacing surface may be an area (such as with a ball and socket configuration), a line (such as with a roller or sleeve bearing), or a point (such as with a ball bearing).

The materials used for different embodiments of the invention will depend to some extent upon the type of surface contact being used as well as the type and extent of wear that may result. Examples of materials that may be used include, but are not limited to polyethylene (or other elastomeric material) on metal, metal on metal, or ceramic on ceramic.

The present invention also allows for customization of the instantaneous axis of rotation (IAR) and/or the center of rotation (COR) of one vertebral body with reference to another. The IAR and COR of a healthy vertebral body with respect to another is constantly changing in all planes because of pushing, pulling, and tethering of the segment through its range of motion by the ligaments, annulus, muscles, facets and other portions of the spine. Often, prosthetic disc replacement designs fail to mimic this varying IAR and COR. For example, a fixed ball and socket has a fixed IAR and COR. One potentially adverse result from using a prosthetic disc having a constrained implant is that the device may cause damage to facet joints due to anatomical interferences that may occur with a fixed axis of rotation. On the other hand, in general constrained IAR systems have been more stable than past designs utilizing a moving IAR. One example of a prosthetic disc having a fixed IAR is described in U.S. Pat. No. 5,314,477.

Conversely, past devices utilizing a moving IAR have provided the advantage of allowing for shear translation and of at least partially mimicking of the moving IAR of a healthy spine. These advantages, however, typically have been achieved in the past at the expense of a loss of stability of the device. Some examples of prosthetic disc designs having a moving IAR are described in U.S. Pat. Nos. 4,759,766, 5,401, 269, and 6,414,551.

In contrast, the present invention allows for an implant design that can mimic or partially mimic this varying IAR and COR to the extent desired by a physician while also preserving stability of the device. For example, one embodiment of the invention is a prosthetic disc that provides a moving IAR substantially in the sagittal plane so that a patient can more easily flex and extent the spine while limiting the movement of the IAR under lateral bending. It is believed that this configuration provides the best of both worlds by allowing a moving IAR for the predominant or more common motion a patient may undertake in day-to-day life while limiting lateral bending to achieve greater stability to the device. Several embodiments of the invention permit translation of one vertebral body with respect to another. By allowing one of these members to translate in the transverse plane results in the IAR and COR also translating in the transverse plane. As explained further below, one additional way of achieving a varying IAR and/or COR in three dimensional space is by combining two articulating surfaces opposing one another.

The interfacing surfaces of articulating and non-articulating embodiments of the present invention also allow for varying degrees of rotational and linear translation, and several embodiments of the present invention likewise permit a similar range of rotation and linear translation. Rotational translation is the movement of the intervertebral segment as a result of movement such as flexion, extension, and lateral bending. There are two components in this translation: one in the cranial/caudal direction and one in the transverse plane. Linear translation is translation in the transverse plane as a result of shear forces applied to the intervertebral segment. Thus, a ball and socket mechanism fixed in one location relative to the intervertebral segment would allow only rotational translation but would not permit linear translation. As illustrated in many of the embodiments that follow, however, linear translation of a ball and socket configuration could be achieved if the ball and socket were able to move in the transverse plane.

Endplates are used to associate the prosthetic disc with the vertebral bodies neighboring the disc. The endplates may be configured in several ways to help ensure a desired endplate-bone interface. For instance, the endplates may have one or more keels that extend into the bony portion of the vertebral body. Over time, bony ingrowth will surround the endplate and further help secure the endplate to the vertebral body.

In addition to keels, the endplate may have other or additional geometry that helps securely hold the endplate in place. For example, the end plate may have one or more teeth, rails, ribs, flanges, or other configurations that can help provide a surface that can secure the endplate more readily to the bone. Other short-term fixation may include screws or other fasteners that hold the end plate to the vertebral body. In some embodiments, these fasteners may be removed once a more long-term interface has been established, or alternatively the fasteners may remain in place indefinitely or until the prosthetic disc needs adjustment and/or replacement.

In addition to providing an endplate surface geometry or configuration that may promote bony ingrowth to securely hold the interfacing surfaces together over the long term, these configurations also may help provide short term fixation of the endplate to the vertebral body. For example, a keel may have a wedge shape so that the width of a first end of the keel near the endplate is narrower than the width of the distal end. Once installed, the inverted wedge of the keel helps prevent separation of the endplate from the vertebral body at least until bony ingrowth can more securely hold the endplate in place.

To help accelerate and to further promote bony ingrowth at the interface between the vertebral body and the end plate, the end plate may be coated with an osteoconductive material and/or have a porous or macrotexture surface. For example, the end plate may be treated with a coating that promotes bone growth. Examples of such coatings include, without limitation, hydroxyl appetite coatings, titanium plasma sprays, sintered beads, or titanium porous coatings.

FIG. 1A is a side view of a posterior prosthetic spinal disc 1 located between sequentially aligned vertebral bodies 2 and 3, such as are found in the cervical, thoracic and lumbar spine. Posterior prosthetic spinal disc 1 conforms in size and shape with the spinal disc that it replaces and restores disc height and the natural curvature of the spine. Posterior prosthetic spinal disc 1 comprises two opposite end plate 5 and 7 which are disposed in two substantially parallel horizontal planes when it is at rest, i.e., when it is not subjected to any load, either moderate or heavy.

The outer faces of end plates 5 and 7 are in direct contact with vertebral bodies 2 and 3 and may be textured or have a plurality of teeth to ensure sufficient contact and anchoring to the vertebral bodies 2 and 3. The outer faces of end plates 5 and 7 may also have a porous or macrotexture surface that facilitates bone ingrowth so that the posterior prosthetic spinal disc 1 is firmly affixed to vertebral bodies 2 and 3. Attached to the inner faces of end plates 5 and 7 are seating members 9 and 11 and a core 13 is securely placed between seating members 9 and 11. A stop member 15 is formed around the equator of the core 13, which functions to limit the motion of vertebral bodies 2 and 3 beyond a predetermined limit that is deemed unsafe to the patient.

As shown in FIG. 1A, the stop member may be formed from a ridge of material found on the core 13. As the end plates move relative to the core in response to movement of the spine, the stop member may approach or engage with one or both of the end plates to restrict further motion in a particular direction. The stop member may be formed of a relatively rigid material so that additional motion is substantially prevented once engaged against an end plate. Alternatively, the stop material may be made of resilient material that provides some cushioning or flex from deformation of the stop material before the range of motion is fully limited.

While the stop member is shown in FIG. 1A as being on the core 13, it also may be disposed on one or more of the end plates. For instance, the end plates may be configured with raised areas or ridges on its perimeter that engage either with the core or the opposing end plate in order to limit further motion in a particular direction. As mentioned above, the stop member on the end plate may limit motion to a greater degree in one direction than in another. Thus, the stop member may have various shapes and thicknesses to provide a variable range in motion that favors or disfavors movement in particular planes. For example, the stop member may have increased thickness on the side portion of the core to provide a more limited range of lateral motion of the spine while still allowing motion in the posterior/anterior direction.

The motion segment comprises a posterior prosthetic spinal disc 1 and adjacent upper and lower vertebral bodies 2 and 3. The exact contours of the core 13, seating members 9 and 11 and stop member 15 determine the range of motion allowed in flexion and extension, side bending, shear and rotation.

FIG. 1B is a top view of a posterior prosthetic spinal disc 1, showing the top end plate 5 and top seating member 9. The end plates may have various shapes that accommodate posterior insertion which avoids contact with the spinal cord. As shown in FIG. 1B, end plates 5 and 7 may have a substantially irregular elliptical shape or curved convex portion that resembles a kidney-shape. FIG. 2A is a top view of a posterior prosthetic spinal disc 1 being inserted between sequential vertebral bones. The posterior prosthetic spinal disc 1 is guided in place with a first implant holder 17 via an angled posterior approach that ensures that contact with the spinal cord 19 is avoided. The posterior prosthetic spinal disc 1 is generally oriented in line with the longitudinal axis of the first implant holder 17. Once the posterior prosthetic spinal disc 1 safely is maneuvered past the spinal cord 19 and in the desired position over the vertebral body 21, the implant may be turned or rotated so that it is oriented at about 90° to the first implant holder 17, as shown in FIG. 2B. Reorienting the implant may be accomplished in many ways. For example, FIG. 2B shows that a second implant holder 23 may be attached on the contra lateral side of the spinal cord to reposition and distract the implant into its final implanted position. Once the posterior prosthetic spinal disc 1 is in place, the first implant holder 17 and the second implant holder 23 is detached from posterior prosthetic spinal disc 1.

It is preferred that the posterior prosthetic spinal disc 1 closely mimics the mechanical functioning and the various physical attributes of the natural spinal disc that it replaces. In some instances, however, the prosthetic spinal disc may permit a more limited range of motion in one or more directions in order to prevent further spinal injury. In general, the prosthetic spinal disc can help maintain the proper intervertebral spacing, allow for proper range of motion, and provide greater stability. It can also help transmit physiological stress more accurately.

End plates 5 and 7, seating members 9 and 11, core 13 and stop 15 may be composed of a variety of biocompatible materials, including metals, ceramic materials and polymers. Such materials include, but are not limited to, aluminum, alloys, and polyethylene. The outer surfaces of the end plates 5 and 7 may also contain a plurality of teeth, maybe coated with an osteoconductive material, antibiotics or other medicament, or may have a porous or macrotexture surface to help rigidly attach the end plates to the vertebral bodies by promoting the formation of new bony ingrowth. Such materials and features may be used in any of the posterior prosthetic spinal discs described herein.

FIG. 3 is a collapsed posterior prosthetic spinal disc 30 that can be opened via scissor action, in which top end plate 32 and bottom end plate 34 are rotated along a pivot point 36 so that the longitudinal axes of top end plate 32 and bottom end plate 34 are substantially perpendicular. Accordingly, the surface area of the posterior prosthetic spinal disc 30 is increased to facilitate greater spinal support. The posterior prosthetic spinal disc 30 in collapsed form is sufficiently small enough to allow for posterior insertion while avoiding contact with the spinal cord.

FIG. 4 is a posterior prosthetic spinal disc having two segments for each end plate that is inserted separately between vertebral bones and assembled or joined together. The first segment 40 is inserted between the vertebral bones while avoiding contact with spinal cord 19. The second segment 42 is subsequently inserted between the vertebral bones while avoiding contact with spinal cord 19, and assembled or joined with first segment 40, forming an end plate having larger surface area. The first and second segments may be joined in any suitable manner to form an end plate. In one embodiment, (As illustrated in FIG. 5 ), the first segment has one or more protrusions and/or ridges 56 63,73,83 that correspond to depressions, notches, or teeth 58,65,75,85 in the second segment. The joining of the protruding regions of the first segment into the depressions of the second helps secure the two segments together. The same procedure is carried out for the second end plate. The size of the assembled end plates may otherwise be two large to insert between vertebral bones while avoiding contact with spinal cord 19. vertebral bodies while avoiding contact with the spinal cord. In its expanded state, the expandable posterior spinal disco 50 has a larger surface area on en plates 52,62 and 54, which increases the contact area between the expandable posterior spinal disc 50 and the vertebral bones.

Figure 5A:
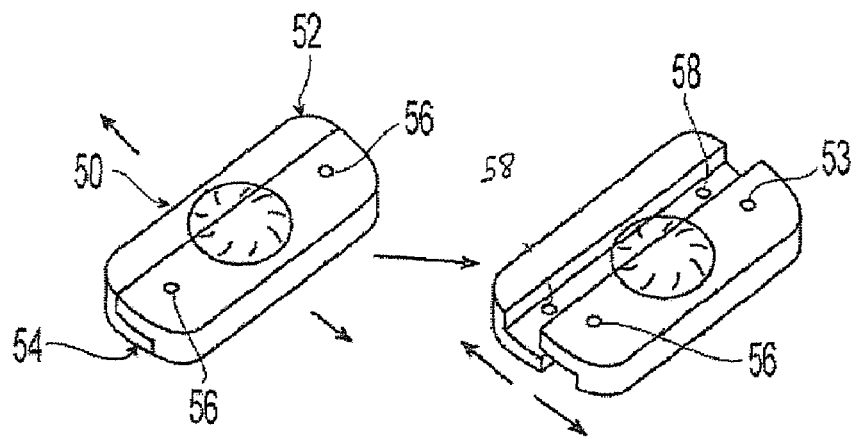
FIGS. 5A-5D depict various expandable posterior prosthetic spinal discs.

FIG. 5A is an expandable posterior spinal disc 50 that comprises expandable end plates 52 and 54 that can expand to increase the contact area of the end plate with the vertebral body onto which it contacts. In its collapsed state, the expandable end plate 52 is small enough to insert between vertebral bodies while avoiding contact with the spinal cord. In its expanded state, the expandable posterior spinal disc 50 has a larger surface area on end plates 52 and 54, which increases the contact area between the expandable posterior spinal disc 50 and the vertebral bones.

The expandable end plate may be formed of two or more segments that provide a low profile when in a collapsed state in order to facilitate a posterior approach during insertion. Once it is positioned over the vertebral body, however, it maybe expanded to increase the surface area of the end plate. The increased surface area helps provide greater stability of the end plate. Expansion of the end plate may be accomplished in several ways. In one embodiment, shown in FIG. 5A, a first segment and second segment may be selectively expanded along a substantially linear edge or surface. Thus, when fully extended the end plate will have a substantially linear slot defined by the edges of the first and second segment edges.

Figure 5B:
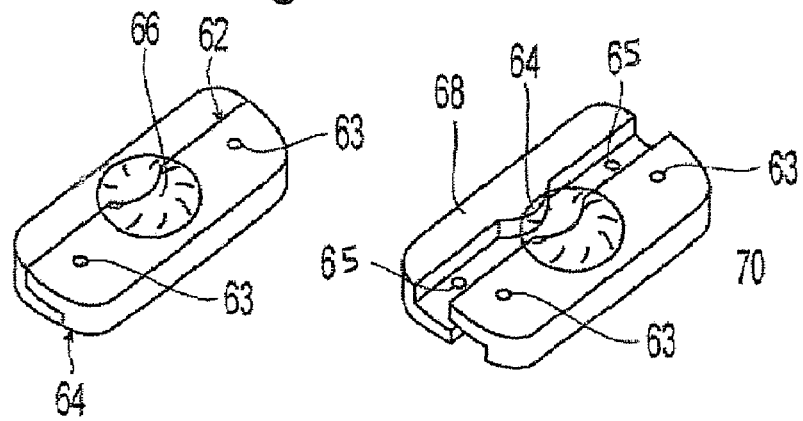

Alternatively, a portion of the edge of the first and second segments may be curved or rounded as shown in FIG. 5B. In this embodiment, the first and second segments may provide more balanced support of the core along its edges or sides. For instance, a curved or rounded portion of the first and second segments may help form a lip 66 that provides extended support of the core on one side than may be achieved from a linear slot. This configuration may help avoid cantilever loading of the core over the slot or opening between the edges of the first and second segments. In other words, lip 66 helps ensure that the connecting portion of the end plate 68 provided more evenly distributed support to the seat member 70.

Figure 5C:
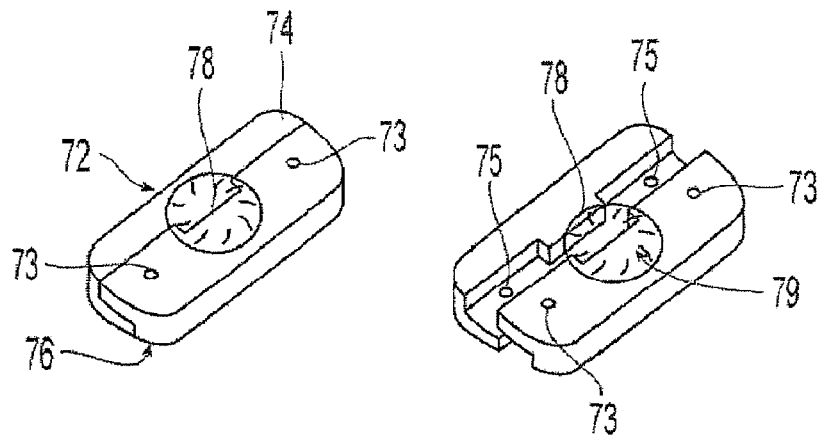
Figure 5D:
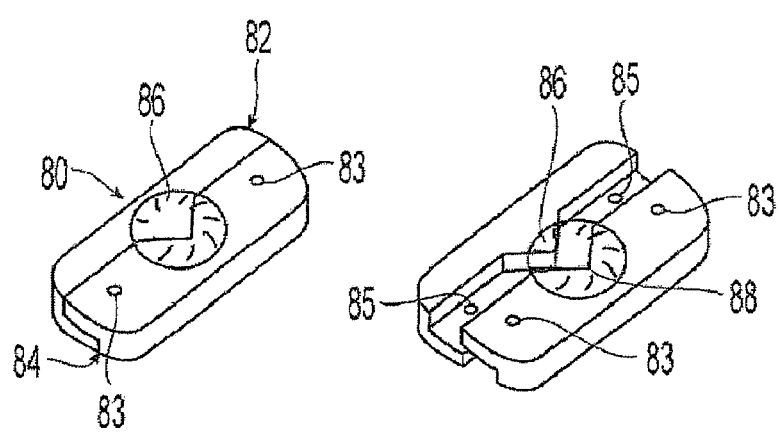

The additional lip 64 of expandable posterior spinal discs can have any shape, provided it is sufficient to reduce the occurrence of cantilever loads. For example, FIG. 5C shows an expandable posterior spinal disc 72 that comprises expandable end plates 74 and 76 that can expand along the latitudinal axis and comprises an additional lip 78 having a rectangular shape on end plate 74 and/or end plate 76. In another example, FIG. 5D shows an expandable posterior spinal disc 80 that comprises expandable end plates 82 and 84 that can expand along the latitudinal axis and comprises an additional lip 86 having a triangular shape on end plate 82 and/or end plate 84. Additionally, a posterior spinal disc may comprise expandable end plates that can expand along the latitudinal axis and comprise an additional lip having a convex curve. In both FIG. 5C and 5D, additional lips 78 and 86 having sufficient overlap with seating members 79 and 88 respectively that facilitates reduction of cantilever loads.

Figure 6A:
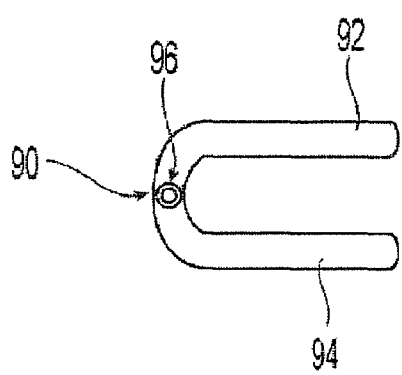
FIGS. 6A and 6B show C-shaped disc implants having a spring.
Figure 6B:
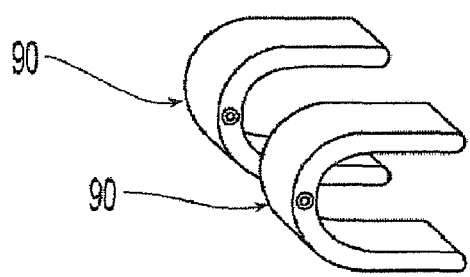

FIG. 6B is a non-articulating posterior prosthetic spinal disc 90 a top end plate 92 and a bottom end plate 94 that are joined together at one end to form a C-shaped disc. A spring 96 is located where top end plate 92 and bottom end plate 94 are joined at one end of each plate 92 and 94 and allow for flexible motion of vertebral bones. The spring can be modified to have various tensions depending on the desired range of motion. The portion that joins the top end plate 92 and bottom end plate 94 also may be flexible itself and, in conjunction with spring 96, facilitates motion of the end plates 92 and 94. FIG. 6B shows two separate non-articulating posterior prosthetic spinal discs 90, both of which can be inserted between the same two vertebral bones. The small size of non-articulating posterior prosthetic spinal discs 90 allows for easy insertion while avoiding contact with the spinal cord, and further provides greater freedom of motion because each non-articulating posterior prosthetic spinal disc 90 functions independently of one another. In general, the non- articulating posterior prosthetic spinal discs encompassed by the invention have a C-shaped design, where openings, slots or springs create flexibility in the material to allow motion.

FIG. 7A shows a C-shaped disc 100 having convexly curved end plates 102 and 104, flexible portion 106, and stops 108. The outer surface of end plates 102 and 104 may contain a plurality of teeth, may be coated with an osteoconductive material, antibiotic, or other medicament, or may have a porous or macrotexture surface to rigidly attach the C-shaped disc to the vertebral bodies and promote formation of new bone. The flexible portion 106 is tapered and the amount of taper controls the flexibility of the C-shaped disc. For example, increasing the amount of taper increases the flexibility of the C-shaped disc. Flexibility may further be controlled by providing a slot 109 located at the flexible portion 106. The slot may be cut in any shape and oriented in any manner within the flexible portion. The size of the slot may be varied to fine tune flexibility. For example, larger slot sizes provide flexibility of C-shaped discs. In another embodiment, more than one slot may be provided to increase flexibility. The stops 108 are located at the end opposite of the flexible portion 106 and limit the motion of the C-shaped disc 100. The size of the stops 108, as well as the amount of curvature of end plates 102 and 104 may be varied to control the range of motion of the end plates before the stops 108 touch. Once the stops 108 touch under moderate loads, the curved end plates 102 and 104 provide another range of motion under heavy loads that flatten and decrease the curvature of end plates 102 and 104.

FIG. 7B shows a C-shaped disc having stops 110 that are convexly curved to provide lateral flexibility. Once the stops 110 touch under moderate load, the curved surface allows the stops 110 to roll in order to facilitate some lateral spinal movement. The curvature of the stops can be varied to provide more or less lateral flexibility. In one embodiment, both stops 110 may be curved. In another embodiment, one stop may be curved while the other stop may be flat, convex, or have a different curvature. The stops also can have other surface shapes that allow for lateral flexibility, such as angled edges. In addition, slots may be formed on the lateral sides of the flexible portion to facilitate movement of end plates 102 and 104 in the lateral plane.

FIG. 8A shows a C-shaped disc 120 having end plates 121 and 122, stops 124, and a flexible portion having an opening 126 and slots 128. Stops 124 are located at the end opposite of the flexible portion and limit the motion of the C-shaped disc 120. The size of the stops 124, as well as the amount of curvature of end plates 121 and 122 may be varied to control the range of motion of the end plates before stops 124 touch. Once stops 124 touch under moderate loads, the curved end plates 121 and 122 provide another range of motion under heavy loads that flatten and decrease the curvature of end plates 121 and 122. The flexible portion contains slots 128 running through the lateral axis and can have any shape. The flexible portion also contains an opening 126 that is bored out along the longitudinal axis and also helps provide flexibility. The number of slots, the size and shape of the slots, and the size and shape of the opening enable fine tuning of flexibility, where, for example, increasing the number of slots, as well as increasing the size of the slots or opening, provide for greater flexibility. In one embodiment, the flexible portion may be located closer to the middle of the disc, forming a skewed H-shaped disc, such as illustrated in FIG. 8B. The H-shaped disc allows for greater flexibility in the anterior and posterior directions. The outer surface of end plates 121 and 122 may contain a plurality of teeth or be coated with an osteoconductive material, have a porous or macrotexture surface to rigidly attach the C-shaped disc to the vertebral bodies, as well as to promote formation of new bone.

Figure 9:
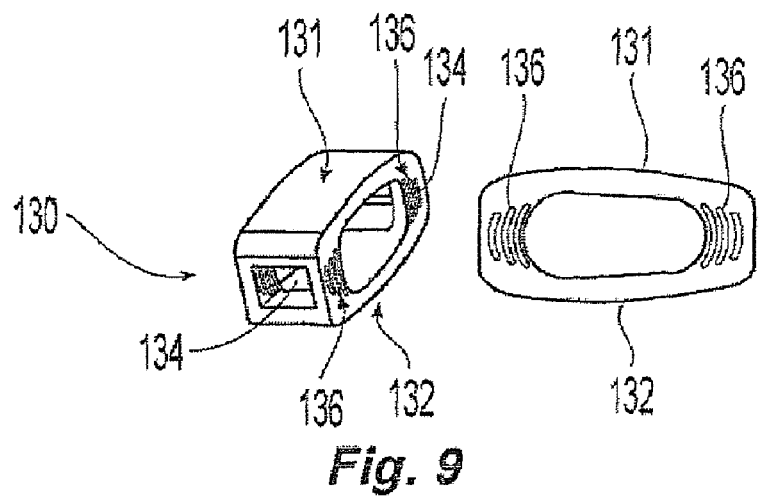
FIG. 9 shows a flat O-shaped disc having two side columns having slots.

FIG. 9 shows a generally oval-shaped or O-shaped disc 130 having end plates 131 and 132 and two flexible portions joining end plates 131 and 132 at the longitudinal ends. Each flexible portion contains slots 136 running through the lateral axis and can have any shape. Each flexible portion also contains an opening 134 that is bored out along the longitudinal axis and also helps provide flexibility. The number of slots, the size and shape of the slots, and the size and the shape of the opening enable fine tuning of flexibility, where, for example, increasing the number of slots, as well as increasing the size of the slots or opening, provides greater flexibility. Each flexible portion may have the same or different configuration of slot shapes, numbers and sizes, positioning, as well as size and shape of the opening. The flexible portions can also be placed near the midline of the disc. In addition, the end plates can have convex curvature such that at heavy loads, the O-disc can flex by decreasing the curvature of end plates 131 and 132. The amount of curvature can be varied to provide different flexibilities. The outer surface of the end plates 131 and 132 may contain a plurality of teeth or be coated with an osteoconductive material, having a porous or macrotecture surface to rigidly attach the C-shaped disc to the vertebral bodies, as well as to promote formation of new bone.

Figure 10:
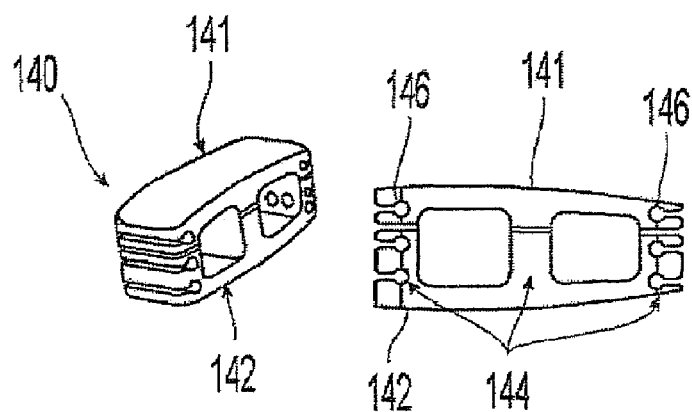
FIG. 10 shows a flat O-shaped disc having an additional column in the center portion of the disc and slots in the outer columns.

FIG. 10 shows a relatively flat double oval 140 or O-shaped disc having an additional column in the center portion of the disc and slots in the outer columns. The disc has end plates 141 and 142, and columns 144 having slots 146 that provide flexibility. With the additional column in the center of the disc, end plates 141 and 142 will have a lesser degree of flex when compared to the O-disc described in FIG. 9. Such a configuration is desirable in applications where a more rigid disc is required. The slots 146 may have any shape, size or positioning and as shown, slots 146 are rectangular notches having a cylindrical hole formed at the inside end of each notch. The outer surface of end plates 141 and 142 may contain a plurality of teeth or be coated with an osteoconductive material, have a porous or macrotexture surface to rigidly attach the C-shaped disc to the vertebral bodies, as well as to promote formation of new bone.

As shown in FIG. 10, the central column may have a gap or opening where the lower portion of the column terminates below the terminus of the upper column. This gap, which in one embodiment can be from about 0.5 mm to about 5 mm, allows the end plates 141 and 142 to have some ability to flex initially until the upper and lower columns meet to prevent further compression. In another embodiment, one or more columns may be formed from a highly resilient material that can provide some limited motion followed by cushioning that increasingly resists further displacement as loading on the prosthetic disc increases.

Figure 11:
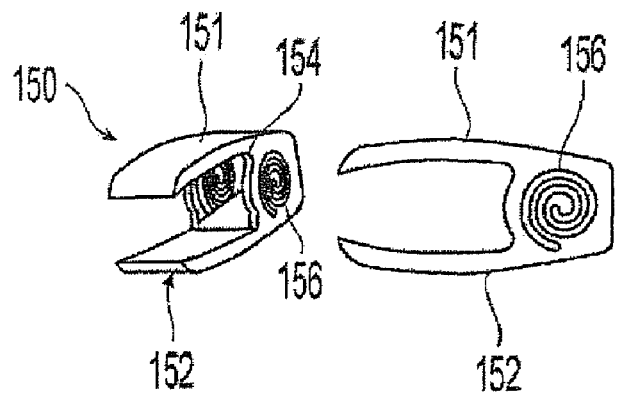
FIG. 11 is a C-shaped disc having a coil slot.
Figure 25:
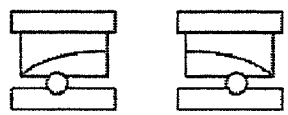
Figure 26:
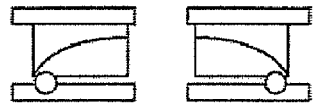

FIG. 11 illustrates another embodiment of the present invention where a C-shaped disc 150 has two end plates 151 and 152, the posterior ends of which are connected by a flexible portion, and the flexible portion, and the flexible portion contains a coil slot 156 and an opening 154 that is formed along the longitudinal axis of the disc. The coil slot 156 and opening 154 that is formed along the longitudinal axis of the disc. The coil slot 156 and opening 154 provide flexibility and can be controlled by varying the size of the coil slot, number of spirals in the coil slot, as well as the size and shape of the opening 154. The outer surface of end plates 151 and 152 may contain a plurality of teeth or be coated with an osteoconductive material, having a porous or macrotexture surface to rigidly attach the C-shaped disc to the vertebral bodies, as well as to promote formation of new bone.

In another embodiment of the invention, illustrated in FIGS. 12-14, utilizes a combination of tensioned and compressed elements disposed between the upper and lower end plates. The tensioned and compressed elements may be springs, as shown in FIG. 13, or may be made of resilient material that provides suitable resistance to stretching or compression. The compression element helps support axial loading along the treated vertebral bodies so that their relative positions approximate a healthy vertebral body supported by a natural disc. Additionally, at least one tension element helps provide controlled bending or movement of the vertebral bodies relative to each other.

The tensioned or compressed elements may likewise be configured and adapted to allow for compression and translation as shown in FIG. 12. Referring to FIGS. 13 and 14, the compression element can be pivotally connected to the upper and lower end plates, thereby allowing translation of the end plates in at least one direction by rotating the compressed element about the pivots. FIG. 14 shows that additional translation can also be provided in a second direction by configuring the pivoting connection such that the compressed element may slide along a rod or bar connected to one or more of end plates. As shown in FIG. 13, the first and second direction of translation can be generally orthogonal to each other. In this manner, a limited degree of translation permitted in any direction can be accomplished without affecting the range of translational motion in the second direction.

FIGS. 15-20 illustrate another embodiment of the invention including two or more implants that complement each other to form an arced or curved surface in the medial-lateral direction and in the anterior-posterior direction. FIG. 15 illustrates the curvature created in the medial-lateral direction, while FIG. 16 shows the curvature created in the anterior-posterior direction. As shown in FIGS. 17 and 18, the complementary curved surfaces of the upper and lower portions of the implants allows the upper vertebral body to move relative to the lower vertebral body while also maintaining a distance between the bodies that approximates the height of a natural disc.

The implants may be space close together or far apart according to factors such as the size of the vertebral bodies, the loading that the implants will undergo, and the range of motion desired. As the implants are moved either closer together or farther apart, however, the curvature of the sliding surfaces may be changed. For instance, in the embodiment shown in FIG. 18, the curvature of the upper and lower portions of the implants in the lateral-medial direction is based on a radius R1 or R2. For implants separated further apart, the radius R2 is larger to account for the increased space between the implants. Changing the radius R according to the spacing between the implants helps maintain a relatively uniform radius of curvature across the full length of the implants.

Referring to FIGS. 19 and 20, the upper and/or lower portions of the implants may have stops to help limit motion in one or more directions. As shown in FIG. 19, for example, medial-lateral movement can be controlled or limited by including a stop on one or more sides of an upper or lower portion of the implant. As the stop engages with the opposing surface of the implant, further movement in that direction is restricted. Alternatively, a resilient material may be disposed between the stop and the opposing surface in order to provide cushioning and to allow resistance to further movement to progressively increase. FIG. 20 illustrates that stops may be similarly used on one or more sides of the implant to limit the range of motion in the anterior-posterior direction. While the stops in FIGS. 19 and 20 are illustrated protruding upwards or downwards, there are many other configurations that may be used to create a stop or to limit motion. For instance, the sliding surface of the portions of the implants may be prevented from further movement simply by contacting the end plate of the opposing portion.

FIGS. 21-26 illustrate one embodiment of the invention where different surfaces of the prosthetic disc provide for different types of movement. For instance, upper portion indicated as B in FIG. 22 may be configured so that the interfacing surface permits only lateral bending, while the lower portion A may have an interfacing surface that is a ball or radiused rail that can translate for axial rotation.

Normally, during lateral bending the space between one side of neighboring vertebral bodies becomes larger while the space between the opposite side of the neighboring vertebral bodies gets smaller. One embodiment of the present invention helps mimic this characteristic of lateral bending by using a plurality of implants with upper and lower portions separated by oblong inserts.

Figure 27:
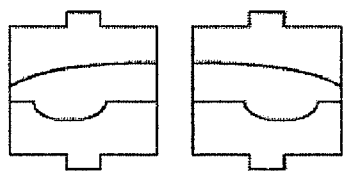
FIGS. 27-29 illustrate one embodiment of the invention using oblong inserts.
Figure 28:

As shown in FIG. 28, the oblong inserts are configured within the upper and lower portions of the implants at an angle so that during bending one insert rotates to help raise one lateral side while the other insert rotates in the same direction to help lower the opposing lateral side. To accomplish this combination of rising and lower of opposing sides of the vertebral body during lateral bending, the oblong inserts are positioned such that the upper ends of the insert are further apart than the lower ends Preferably, the oblong inserts are positioned such that they are angled from abut 5° to about 20° from a vertical axis when the vertebral bodies are in a neutral position, i.e., under conditions when there is no lateral bending. More preferably, the oblong inserts are positioned such that the axis from the upper end to the lower end is from about 70 to about 130 off of a vertical axis when the vertebral bodies are in a neutral position. As shown in FIG. 27, the insert on the opposing side of the vertebral body is positioned at approximately the same angle, but at a mirror image of the first insert. In this manner, one side will become lower during lateral binding while the opposing side increases in height.

The amount of increase or decrease in height from rotation of the inserts during lateral bending can be controlled in part by the length of the inserts from the upper end to the lower end. Thus, a longer insert will permit a greater range of lifting or lowering than a shorter insert. In one embodiment, the length of the insert is from about 3 mm to about 15 mm. In another embodiment, the length of the insert is from about 5 mm to about 10 mm.

Figure 29:
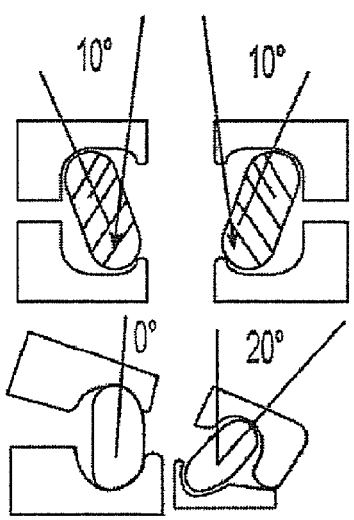

Additionally, the angle at which the inserts are initially positioned when the vertebral bodies are in a neutral position will also affect the degree to which there is a rise or fall in height from rotation of the inserts during lateral bending. For example, inserts that are angled only slightly off of a vertical axis will only be able to slightly raise or lower the height of the sides, whereas increasing the initial angle off of the vertical axis will allow more significant differences in height to occur. Thus, it is possible to control the degree of increase or decrease of height during lateral bending at least by either changing the length of the inserts or by changing the angle at which the inserts are positioned. For example, for the configuration shown in FIG. 29, the inserts may be positioned such that they are about 100 off of a vertical axis when the vertebral bodies are in a neutral position. In another embodiment, the angle may be from about 3° to about 150.

Figure 30:
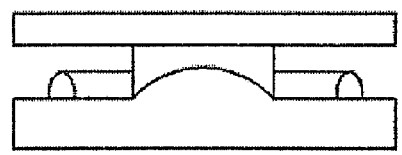

As discussed previously, the contacting surfaces of the upper and lower portions of an insert may be configured to have curved surfaces that allow varying degrees of lateral-medial movement or posterior-anterior movement. Stops also may be used to help further control or restrict movement. In addition to these features, stiffness mechanisms also may be used to provide greater resistance to movement. FIG. 30, for example, illustrates an upper and lower portion of an insert. A ring of elastomer is disposed in the space where the surfaces of the upper and lower insert meet. When compressed, the ring of elastomer adds non-linear resistance.

Figure 31:
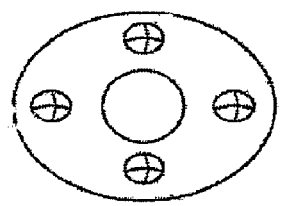
Figure 32:
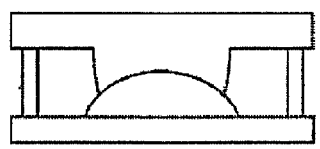

The use of elastomer to provide non-linear resistance to compression may be used in a wide variety of configurations in addition to a ring. In FIG. 31, for example, a plurality of elastomer protrusions or nubs may be used to add stiffness or non-linear resistance to compression. Skilled artisans would likewise appreciate that other materials or structures may be used to increase resistance to compression. For example, one or more of elastomer nubs or protrusions in FIG. 31 may be replaced with springs. Further illustration of this embodiment is shown in FIG. 32, where springs and/or elastomer can be placed in tension at various locations between the upper and lower portions of the insert.

Yet another variation of this embodiment is to use one or more flexible cantilevers to provide increased stiffness or resistance to compression. Referring to FIG. 33, one or more rods may extend from one portion of an insert, i.e., an upper or lower portion, toward the surface of the opposing portion of the insert. In one embodiment, one end of each rod is fixed to a portion of the insert, but is not fixed to the other portion of the insert.

Thus, one end is fixed to one portion of the insert while the other end is free to move or bend in response to loading. The free end may be in contact with the surface of the opposing portion of the insert or alternatively may be preloaded by pressing it against the surface of the opposing portion of the insert. In another embodiment, the free end does not contact the surface of the opposing portion of the insert until a predetermined amount of movement of one portion relative to the other has already occurred.

Once the free end contacts the opposing surface, the bar will begin to bend in response to additional movement. As the bar bends, the bending forces resist any further movement or compression, and as the movement in a particular direction increases, the resistance increases as well.

As shown in FIG. 33, the free end may be curved, bent, or otherwise shaped to prevent premature wear of the surface of the opposing portion. The flexibility of each cantilever rod may be altered or adjusted to allow greater or more rapid resistance to motion in one direction than in another. For instance, cantilever rods placed to resist lateral bending may be more flexible or less resistant to movement than a cantilever rod used to resist anterior-posterior movement.

The cantilever rods also may be used to provide controlled resistance to rotational movement of the vertebral bodies. FIG. 34 shows a top view of an insert having this embodiment of the invention. Mechanical stops may be disposed near the free ends of the cantilever rods so that once rotation increases beyond a certain point the free end engages with one of the stops and causes the cantilever bar to bend or resist further rotational movement. The torsional resistance created from the stops increases as rotation continues.

Another embodiment of the invention utilizes a flexible rod or shape memory metal rod near the center of the insert to provide a stop or to generate progressive resistance to flexing, extension, lateral bending, or rotation. One example of this embodiment is shown in FIG. 35, which illustrates a rod connected to a lower portion of an insert and extending upwards into a cavity of the upper portion of the insert. As with any of the embodiments described herein, the upper and lower portions of the insert may be configured to have a ball and socket configuration or a simple radius protruding portion and corresponding simple radius receiving portion, thereby permitting lateral-medial movement, anterior-posterior movement, and rotational movement.

As the upper portion of the insert moves, the cavity wall eventually will contact the free end of the rod. If the rod is very stiff, contact with the cavity wall will stop further movement. In contrast, if the rod is flexible, it may bend in response to contact with the cavity wall, thereby providing progressive resistance to further movement in that direction.

The cross-sectional profile of the cantilever rods described herein may be any shape, and are not limited to circular cross-sections. For instance, the cantilever bars may have a generally rectangular cross-section so that it is more resilient to bending loads in one direction than in another.

Different cross-sectional shapes also may be used to provide resistance to rotational movement in the embodiment illustrated in FIG. 35. For instance, if the cantilever rod has a rectangular cross-section as illustrated in FIG. 36, and extends into a non-circular cavity, rotational movement can cause the free end of the cantilever to contact the cavity wall. Once again, the stiffness of the cantilever can be varied to either prevent further rotation beyond a certain point (i.e., the cantilever acts as a full stop to further rotation), or the cantilever can flex or twist to provide progressively increasing resistance to further rotation.

In an alternative embodiment (as depicted in FIG. 37), two or more rods may be disposed within the central portion at spaced apart locations so that rotation causes the plurality of rods to bend and impart torsional resistance to further rotation. FIG. 38 illustrates a socket/ball compression mechanism according to the invention. The hinges may be placed at A to allow the socket/ball to "float".

FIGS. 39-41 show a non-articulating insert according to the invention having two endplates attached to springs, preferably at least 2 or more independent springs. The springs allow for motion (translation), compression, and a combination of both (flexion/extension and lateral bending). As illustrated in FIGS. 42A (showing an axial view of the spine), a single insert may be used with posterior or posterior lateral implantation. In addition, more than one insert may be used, jointly or independently of each other. For example, FIGS. 42B-C shows two inserts implanted through posterior or posterior implantation, whereas FIG. 42D depicts three inserts. Multiple inserts may have the ability to attach to one another after implantation.

Figure 45:
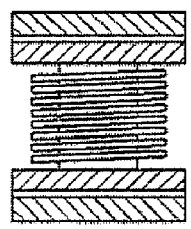

FIGS. 43-45 illustrate an insert where pivots are added to the non-articulating insert of FIGS. 39-41. The pivots allow motion, whereas the springs act as shock absorbers and restore the implant to a neutral position. The endplates may have teeth or other means to secure to the vertebral body.

Figure 46:
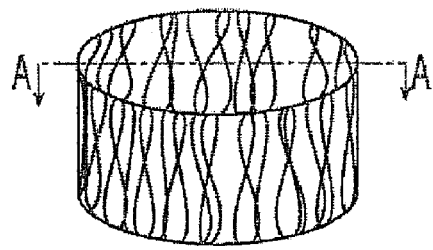
FIGS. 46-47 show one embodiment of the present invention utilizing a braided reinforcing material around a balloon or bladder.
Figure 47:
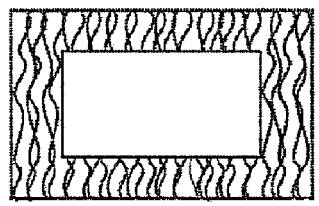

A hollow braid may also be used to make the insert of the invention. As shown in FIGS. 46-47, the braid may be reinforced with metal struts for strength and fixation. In addition, the hollow pocket may be filled with a balloon or a bladder to mimic the annulus or nucleus. The balloon may be filled with air or fluid and can have various shapes, e.g., cylindrical, oval, circular, etc.

The following three examples further illustrate how several of the features described above may be implemented in a prosthetic disc.

Figure 48:
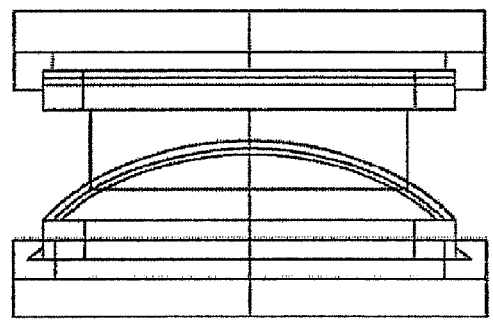
FIGS. 48-50 show one example of the present invention.
Figure 49:
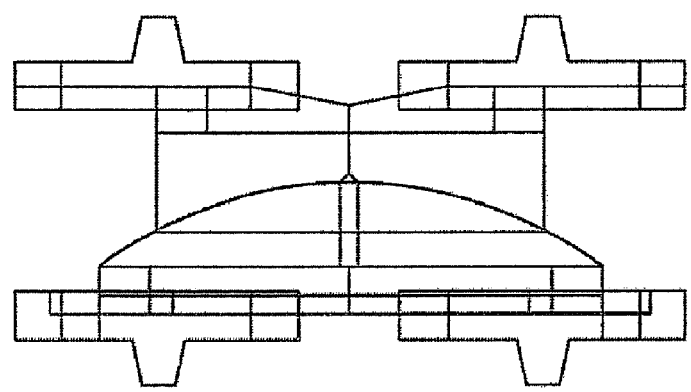
Figure 50A:
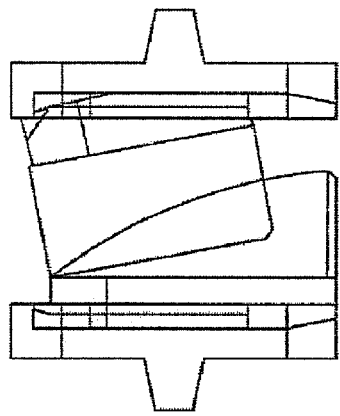
Figure 50B:
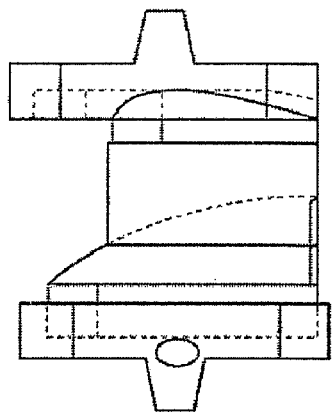
Figure 51:
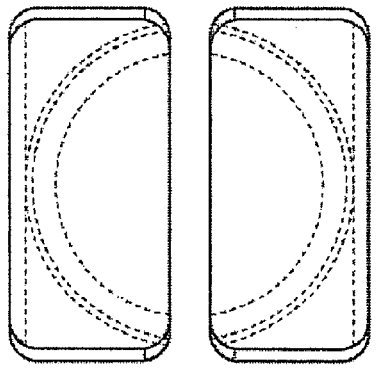
Figure 52:
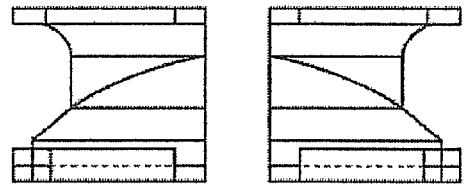
Figure 53:
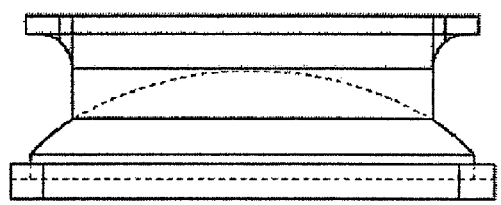

The first example, shown in FIGS. 48 through 50, describes a prosthetic disc that may be designed to have an IAR that is either substantially fixed one location or alternatively may be configured to move in the axial plane. As shown in FIG. 49, a plurality of upper and lower portions may be inserted at spaced apart locations. Preferably, one upper and one lower portion forms an assembly that can be inserted at the same time. By forming the disc from two assemblies as shown in the figures one assembly can be inserted on each side of the spinal cord, thereby greatly reducing the space needed in order to insert the disc. In this manner, many of the risks commonly associated with a posterior approach can be avoided or minimized.

As explained in greater detail below, the upper and lower portions may have segments that can be repositioned after the assembly has been positioned inside the patient in order to bring the interfacing surfaces of the upper and lower portions into their final position.

For example, the upper and/or lower portions may be configured with a movable segment that allows repositioning of the interfacing surface once the portion has been inserted into the patient's body. In this manner, the overall size of the assembly can be made more compact when inserting it into the body while also allowing the components of the assembly to be reconfigured once inside the body in order to achieve optimal positioning of the interfacing surfaces of the prosthetic disc. This, while FIG. 49 illustrates the final positioning of two assemblies after the segments have been repositioned, the segments initially may be inserted into the body in a configuration illustrated in FIG. 50. As shown in FIG. 48, one way to allow repositioning of the segments is to provide a track on which the segments may slide.

The segments may be configured such that they interlock with corresponding segments of a second assembly, as shown for example in FIG. 49. Alternatively, the segments may be configured such that even after repositioning they do not contact a corresponding segment. In any of these embodiments, a locking mechanism may be used to fix the position of the segment relative to the portion it is associated with in order to prevent unintended repositioning of the segment after the surgical procedure is completed. One example of such a locking mechanism is the use of a protrusion or detent.

To further minimize the profile of the assembly during insertion, one segment may be configured such that the assembly has a lower overall height during insertion than when all of the components of the assembly are in their final position within the patient. FIG. 50 illustrates this feature of the invention. In particular, the segment associated with the upper portion of the assembly is configured such that it slides along the interfacing surface of the segment associated with the lower portion of the assembly. The upper portion may be configured with one or more tracks or channels that guide a corresponding number or protrusions or keels on the upper portion of the upper segment. Thus, the upper segment is able to rotate and slide down the surface of the lower segment in order to lower the height of the assembly during insertion. Once inside the body, however, the segment can be slid into its final position. As this occurs, the overall height of the assembly will be increased. In one embodiment the overall height of the assembly may be increased from about 0.1 mm to about 3 mm, and in another the distraction caused by repositioning the segment may be from about 0.5 mm to about 1.5 mm.

The second example of the present invention, illustrated in FIGS. 51 to 54, also uses two assemblies and is configured to have a fixed IAR, the upper and lower portions of the assembly have interfacing surfaces that are substantially spherical in curvature and that have substantially the same radius of curvature so that the overall configuration of the sliding surfaces provides a surface contact over an area as opposed to a line or point. In this example, the assemblies of the upper and lower portions are not configured with slidable segments as described in the example above. Because the sliding surfaces in this example are substantially spherical in curvature, proper alignment of each portion of each assembly is important to achieve a desired surface contact over an area instead of a line or point.

Figure 57:
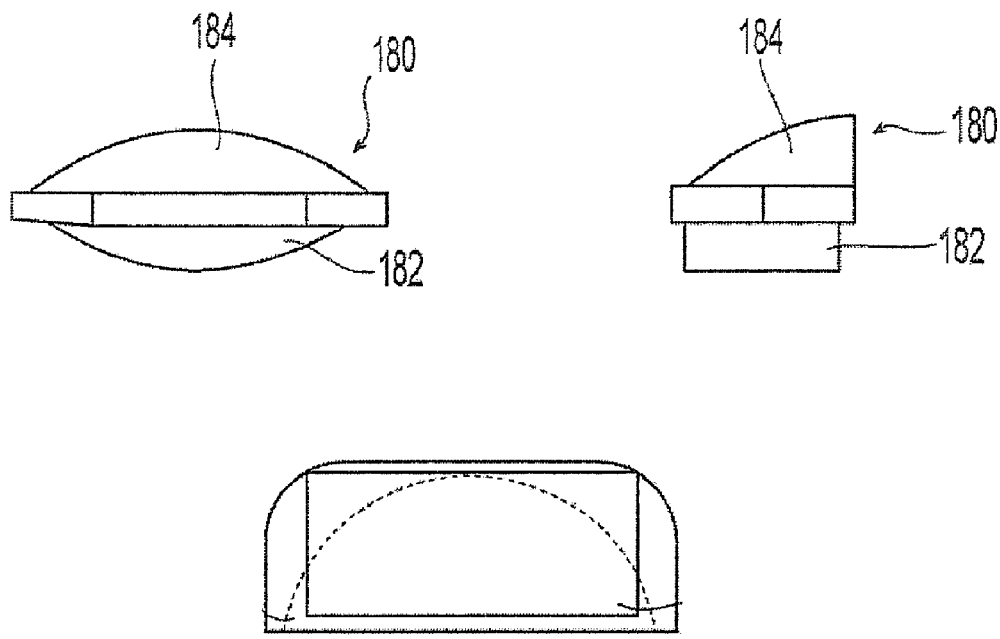
Figure 58:
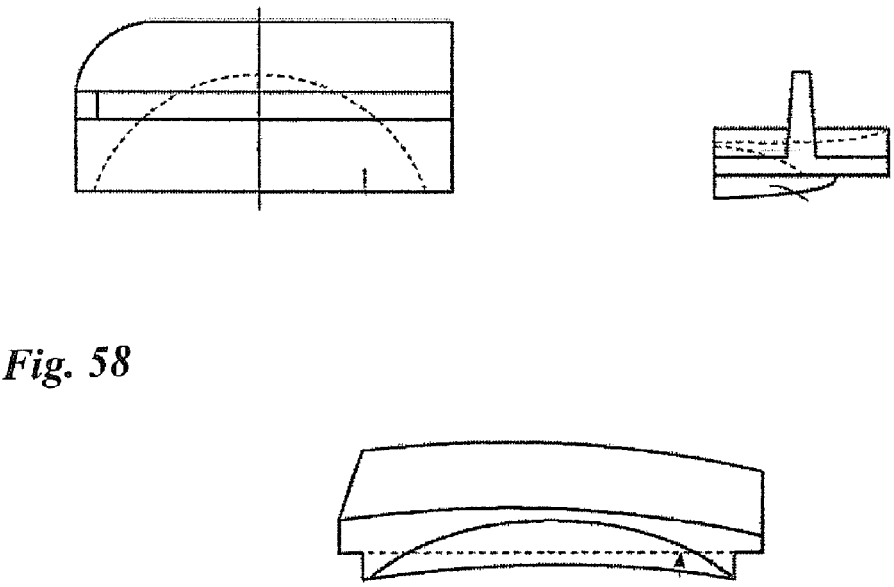

The third example of the present invention is shown in FIGS. 55-61. This example uses two articulating surfaces in a three component assembly to provide a moving IAR in the anterior-posterior direction only. As described in the examples above, two assemblies may be used to provide a low profile during insertion. Each assembly is formed of three components: an upper portion, a lower portion, and a central element having upper and lower surfaces that interface with corresponding surfaces of the upper and lower portions. One interfacing surface is configured in a similar manner as provided in Example 2, above. That is, the interfacing surface is substantially spherical in curvature such that the surface contact is over an area instead of over a line or a point. FIG. 57 illustrates the spherical surface interface disposed between the upper portion and the central element.

The second interfacing surface is formed of two cylindrical surfaces that permit sliding essentially in one direction. Referring again to FIG. 57, the lower surface of the central element has a generally cylindrical shape protruding downward, while the lower portion has a corresponding cylindrical shaped groove formed therein that receives the cylindrical shape of the central element. Preferably, the radii of curvature of both cylindrical shapes are approximately the same such that the surface contact is over an area instead of a line. In this manner, the cylindrical surfaces can be configured to permit bending while restricting rotation. Thus, during flexion or extension both interfacing surfaces permit. movement, while only one interfacing surface may permit lateral bending or axial rotation.

In an alternative embodiment, however, a second cylindrical interfacing surface can be substituted for the spherical surface. This second cylindrical interfacing surface may be disposed orthogonally to the direction of the first cylindrical interfacing surface. In this manner, one surface will permit motion in one direction, such as flexion and extension, while the second will permit lateral bending.

FIGS. 59-61 illustrate the types of motion that may be achieved using a first interfacing surface that is spherical with a second interfacing surface that is generally cylindrical. FIG. 59 illustrates a disc disposed in a neutral position having a disc height H. During extension and flexion, the disc can provide rotational translation in the axial and in the anterior-posterior direction. Under these conditions, the overall height of the disc can change. Additionally, however, the disk also permits linear translation without changing the height of the disk. As shown in FIG. 61, the upper and lower portions can translate with respect to each other without having to also rotate.

Figure 62:
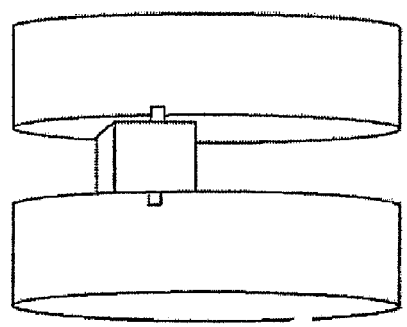
FIGS. 62-65 illustrate the use of a trial for use with several embodiments of the present invention.
Figure 63:
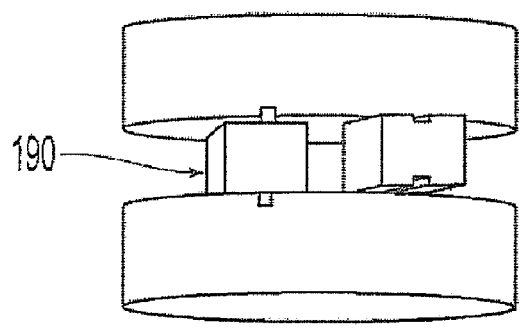

As shown in FIGS. 62A-C, a pair of disc assemblies may be used to form a prosthetic disc of the present invention. One advantage of using multiple assemblies is that a posterior approach may be used to position them into a treated area. A plurality of disc assemblies having varying heights, widths, lengths, and ranges of translation and rotation capability may be provided in a kit to a physician so that the final selection of the proper disc assembly can be made during the surgical procedure. For instance, a plurality of disc assemblies may be provided having disc heights varying from about 10 mm to about 20 mm. In one embodiment, the disc heights may differ by a uniform increment, such as differing by about 1 mm or by about 1.5 mm within a range.

Likewise, the length of the disc assembly may be varied to accommodate different anatomies. For instance, disc assemblies may have longitudinal axes that range from about 20 mm to about 28 mm. Incremental changes in the length of the assemblies may also be provided in a kit, such as by providing disc assemblies of different lengths in 2 mm increments. In another embodiment, a plurality of assemblies may have at least 2 different lengths that differ by more than about 3 mm. For instance, one set of disc assemblies may have a length of about 22 mm, while another set is about 26 mm in length. The length of the disc assembly preferably may be selected so as to maximize implant/endplate contact area.

A plurality of assemblies may also be provided with differing ranges of axial rotation. For instance, one or more assemblies may have no restriction on rotational movement, or may have stops or other devices that prevent rotation only after the rotation has exceeded the range of motion of a natural, healthy spine. Some assemblies may limit a range of axial rotation to $\pm 15°$, $\pm 10°$, $\pm 5°$, or $\pm 2°$.

Other disc assemblies of the present invention may permit a range of axial rotation in one direction, but restrict it in the opposite direction. In other words, a disc assembly of this embodiment may permit limited disc rotation so that a patient may rotate or turn their body to one side or in one direction, but not in the other. For example, a disc assembly may allow rotation or movement between a 0° position, where the spine is not rotated or turned, to up to about 5°, up to about 8°, up to about 10°, or up to about 15° in one direction only.

As described above, a cylindrical surface may be provided in a disc assembly in addition to a second, curved surface corresponding to a portion of a sphere. One feature of this combination of surfaces is that the disc can permit translation between the upper vertebral body and the lower vertebral body neighboring the treated area.

Figure 62D:
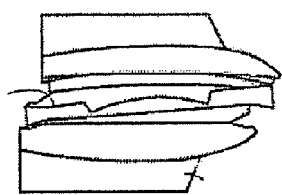

In one embodiment, the disc is capable of permitting translation of up to about 3.0 mm in the anterior-posterior direction, while in another embodiment the disc is capable of translation of up to about 5 mm. Some disc assemblies may permit even more translation, such as up to about 7 mm or even up to about 10 mm. As illustrated in FIGS. 62C and 62D and described in depth above, mechanical stops may be provided to limit the range of motion of the disc assembly. FIG. 62C also illustrates that spacing of multiple assemblies may be important for providing a spherical surface, if one is provided.

The upper and lower portions of a disc assembly may be configured with a keel that can engage with or contact a neighboring vertebral body. One advantage of providing a keel is that is may be used to guide the assembly into position during insertion into a treted area of the spind. For instance, a channel or groove may be cut out of a vertebral body next to the treated area. Then, a physician may insert the assembly into the vertebral body so that the keel slides in the groove or channel. the keel and grove or channel may be substantially linear or straight, or alternatively, may be curved or arched so that the assembly rotates and slides into position.

The use of one or more keels may also increase bone to implant surface contact, thereby decreasing the likelihood that the assembly will shift or move about of position. In one embodiment, the the increase in surface contact may be about 5% or more, which in another embodiment the increase may be about 15% or more.

Figure 63A:
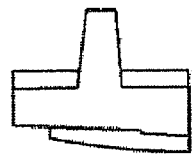

The cross-sectional profile of the keel may have different shapes. For instance, the cross-sectional profile of the keel may have the shape of a wedge, a truncated wedge, a rectangle, or a square. As shown in FIG. 63A, the channel or groove may be cut to have a cross-sectional profile corresponding approximately to the shape of the keel. One advantage of the keel having a truncated wedge cross-section is that a similarly shaped channel or groove may ensure that the keel engages with the bony surface. This configuration may also provide increased resistance to expulsion of the disc assembly.

Over time, it is believe that the stability of the disc assembly in the treated area will further increase as bone growth engages with outer surfaces of the disc assembly. To facilitate this growth and increased stability, all or part of the surfaces of the disc assembly that engages or otherwise contacts bone may be treated to promote bony on-growth. For instance, titanium plasma may be provided on the keel or other portions of the assembly to provide a matrix for bone growth. In addition, the keel may be configured with notches, slots, or openings formed along its length. As bone grows into these openings, the disc assembly will become more securely anchored in place.

Figure 63B:
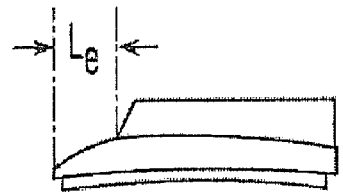
Figure 69:
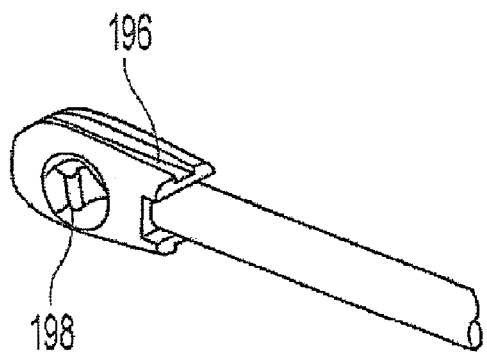

As a disc assembly is first inserted into a treate area, it may need to be repositioned, rotated or otherwise moved. For instance, repositioning the disc assembly may be needed so that the keel can properly engage with the channel or groove. As shown in FIG. 63B, the leading edge $L_e$ of the disc assembly may be configured to not have a keel. Thus, in one embodiment the assembly can be partially inserted into the treated area without the keel engaging with or contacting the vertebral body. In one embodiment, the length of the leading edge is from about 1 mm to about 10 mm, while in another embodiment the leading edge is from about 2 mm to about 5 mm. Alternatively, the length of the leading edge may be from about 1% to about 20% of the length of the component on which it is disposed, or may be from about 2% to about 10%. The length of the component may be determined by measuring the longitudinal central axis of the portion or component on which the leading edge is disposed.

In addition, referring again to FIG. 63B, the keel may have an initial portion that is sloped or gradually increases in height. Providing a ramped portion may aid in aligning and inserting the keel into a groove or channel formed in a vertebral body.

The present invention also encompasses a method for implanting a posterior prosthetic spinal disc. In particular, the method comprises removing a defective vertebral disc using conventional methods and instruments; separating or distracting adjacent vertebral bodies to permit insertion of the posterior prosthetic spinal disc; inserting and positioning the posterior prosthetic spinal disc using a posterior or posterior lateral insertion that avoids contact with the spinal cord; and relieving the separation or distraction of the adjacent vertebral bodies.

As will be explained in greater detail below, there are several variations in which the present invention may be used to provide a replacement or prosthetic disc for a patient that restores or maintains a more natural range of motion. While a single disc assembly may be used to establish the artificial disc within a patient, it may be preferred in some cases to provide more than one artificial disc assembly. Vertebral bodies having large-sized endplates, for instance, may benefit from using two or more disc assemblies, or subassemblies to create an artificial disc in a treated area. For example, a disc assembly that is from about 9 mm wide may only need an insertion window that is from about 9 mm to about 11 mm of wide. In one embodiment, the insertion window needed to deploy a disc assembly is from about 7 mm to about 15 mm wide, and more preferably is from about 9 mm to about 12 mm wide.

There are several benefits that may be realized from using multiple disc assemblies. For instance, one result of using multiple assemblies may be that the smaller insertion windows may not require as significant motion or retraction of the aorta or vena cava. For example, in one embodiment, movement of the aorta in the present invention for inserting one of a plurality of disc assemblies is less than half the distance of repositioning that would be required if the prosthetic disc were made of a single, full size assembly. In addition, using multiple disc assemblies may allow a shorter duration of time during which the aorta, vena cava or other anatomy is moved out of its natural position. In one embodiment, for example, the duration of time that the aorta or vena cava is moved for inserting one or a plurality of disc assemblies is less than half of the duration of time normally required to insert a prosthetic disc made of only one assembly or unit. Also, the smaller insertion windows that can be achieved from using multiple disc assemblies will likely make it easier to access the disc space from as well as allow for greater options in the approaches that may be used.

Furthermore, the use of multiple assemblies may reduce the frequency and/or the amount of retraction needed during insertion and positioning of the assemblies. For example, if two disc assemblies are used in a posterior approach, a central region of the treated area in the anterior-posterior direction may have sufficient space for placing a distractor. As a result, other benefits from this configuration may also be achieved. For instance, in many embodiments of the invention it may be useful to ensure that the prosthetic disc is positioned properly along the midline of the vertebral body in the anterior-posterior direction. By using a distractor in the central region of the treated area, the present invention may allow a physician to select a midline of the prosthetic disc with respect to the vertebral body, distract the vertebral bodies with the distractor in the central region, conduct an x-ray or other procedure to confirm that the selected midline of the prosthetic disc is approximately the same as the midline of the vertebral body, and make any desired adjustments of the distractor location before inserting a disc assembly. In one embodiment, the physician's selected location of the midline of the prosthetic disc differs from the midline of the vertebral body by less than about 3 mm, and more preferably differs by less than about 1 mm at any point along the length of the part of the distractor located between the vertebral bodies. If the difference between the selected location of the midline of the prosthetic disc and the confirmed midline of the vertebral body falls outside an acceptable tolerance, the physician may then reposition the distractor and either reconfirm its new position or continue with inserting the disc assemblies after the adjustment is made. Once the distractor is in an acceptable or desired position, the disc assemblies may then be placed within the treated areas. The distractor location may be used with or without other tools or devices to help ensure correct placement of the assemblies with respect to the anterior-posterior midline of the vertebral bodies.

A disc assembly may comprise three component parts: an upper rigid plate, a lower rigid plate, and a central core or core element. The core element is disposed generally between seating surfaces of the upper and lower plates. The seating surfaces of each plate may be contoured to provide a desired range of motion. For example, one or more of the seating surfaces may have a substantially spherical curvature. In this manner, the seating surface may generally correspond to a portion of a ball or a socket. The central element may likewise have a contoured surface that generally has the same curvature as the seating surface it contacts. Thus a spherical-shaped seating surface can receive or contact a portion of the central element having a spherical contour having a similar radius of curvature. The contact between the two surfaces may therefore correspond to a portion of a ball and socket.

Providing a spherical surface allows the two component to rotate and slide across the contacting surfaces in a manner that would permit bending and rotation of one vertebral body relative to another. If these two contacting surfaces were the only elements allowing movement, the IAR of the disc would be constant. Providing a second contacting surface allows the disc to mimic a variable IAR of a healthy disc. For example, a second contacting surface between the second rigid plate and the central element may have a cylindrical contour, preferably allowing the core element to provide rotation in the anterior-posterior direction. Thus, it is preferred that the cylindrical surfaces of the second rigid plate and core element have an axis of rotation that extends approximately in a lateral direction.

The combination of a spherical shaped surface contact between one plate and a portion of the core element with a second generally cylindrical contacting surface between another plate and another portion of the core element allows the disc to have a variable IAR. This configuration also allows for translation of one vertebral body relative to another vertebral body without requiring either vertebral body to rotate and without requiring the distance between the vertebral bodies to increase or decrease.

The curvature of the seating surfaces of the plates may be concave and the corresponding contoured portions of the core element may be convex to provide contact between the surfaces. Alternatively, one or more of the contoured surfaces of the core element may be concave and the seating surface for which it engages likewise may be inverted. For example, in one embodiment the core element may have a contoured convex surface that it semi-spherical or generally corresponds to a portion of a spherical surface, and a contoured concave surface that is semi-cylindrical or generally corresponds to a portion of a cylinder. One advantage of this configuration is that is may be capable of achieving a lower overall height than a core element having two convex contoured surfaces.

As described previously, more than one assembly may be used to form a disc. For example, a second assembly may be provided having a similar arrangement of plates and a core element. When disposed in a treated area, one or more components of one assemblies may contact or even interlock with a corresponding component of another assembly. For instance, the seating surfaces of plates disposed on the bottom of two assemblies may be independently inserted into the treated region and subsequently joined. Conversely, the assemblies may be disposed at a predetermined distance from the other. For example, if two or more assemblies have contoured semi-spherical surfaces with a large radius of curvature, the assemblies may be separated by a predetermined distance so that the two contacting surfaces operate as component parts of a ball and socket configuration.

The configuration of the contacting surfaces of the disc may be varied depending upon the surgical approach used to insert the assembly. For instance, in one embodiment a facet capsule may be removed from one side of a vertebral body to provide access to the treated area from a transforaminal approach. The endplates of the vertebral bodies in the treated area may then be cut or otherwise prepared for receiving an assembly. Preferably, the bony anatomy of the vertebral body that defines the vertebral foramen still encloses this region after the removal of the facet capsule. Once the treated area is prepared, an assembly may be inserted. In addition to a posterior or transforaminal approach, other approaches can be used with the present invention, including, but not limited to posterior-lateral, lateral, or anterior approaches.

With a transforaminal approach, the direction or path in which the assembly is inserted may form an angle with an axis extending in the anterior-posterior direction. Because the approach to the treated area is at an angle, the seating surfaces may be configured to provide a desired functionality. For example, as described above, the assembly may have a cylindrical seating surface having an axis that extends generally in a lateral direction of the spine. Thus, the plates of the assembly may have a longitudinal axis that generally corresponds to the path in which the assembly is inserted, and the axis of rotation of the cylindrical contoured surface of the core element may form an angle from about 20° to about 70° of the longitudinal axis. More preferably, the angle between the longitudinal axis of the plate and the core element axis of rotation forms an angle from about 30° to about 60°.

When a facet capsule is removed, the rotational stability of the vertebral body may be compromised. Since anatomy that helps prevent excessive rotation of the vertebral body is removed, it may be beneficial to provide a mechanical stop that prevents rotation in the compromised direction. In one embodiment, the stop only permits rotation of less than 10 degrees in one direction, and more preferably prevents rotation greater than 7 degrees. In other embodiments, the stop only permits rotation from about 1 to about 7 degrees, or from about 1 to about 5 degrees in one direction. If the facet capsule on the opposing side of the vertebral body is still intact, it may not be necessary to provide a mechanical stop for rotation in the opposite direction. In this manner, a rotational stop may be provided only when anatomy aiding in this functionality has been removed.

It is preferred that the contact between the seating surface of a plate and a contoured surface of a core element extends over an area rather than a line or a point. More preferably all contact surfaces of the invention extend over an area. However, if a convex surface semi-spherical surface is formed with a smaller radius of curvature than the corresponding concave surface, it would be possible to have the contact between the two surfaces correspond to a point contact. Likewise, a convex cylindrical surface may be formed to be smaller than the concave cylindrical surface it engages with in order to form a contact surface corresponding to a line.

The plates also may be configured to better engage with the vertebral bodies that they contact. For instance, one or more raised ridges or keels may extend at least partially into the endplate of the vertebral body. The vertebral body likewise may be prepared by cutting a similar number of grooves or channels that will receive the keels. The grooves or channels may help guide the assembly into proper position in the treated area. This feature may be particularly beneficial when a certain orientation of the assembly relative to the vertebral body is desired.

The ridges or keels and corresponding channels or grooves also may be straight or curved to match the desired insertion path of the assembly. In one embodiment, the cross-section of a ridge or keel may be triangular or have a truncated triangular shape. As mentioned above, if more than one assembly is being used, it may be desirable for the assemblies to be separated by a predetermined distance. The grooves or channels formed in a vertebral body may help achieve the proper orientation and distance of the assemblies.

Figure 64:
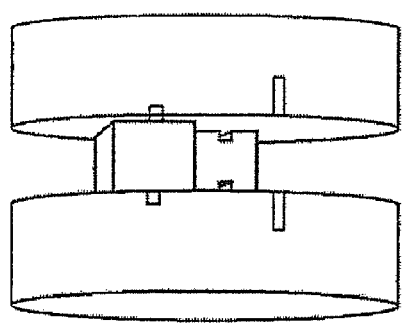
Figure 65:
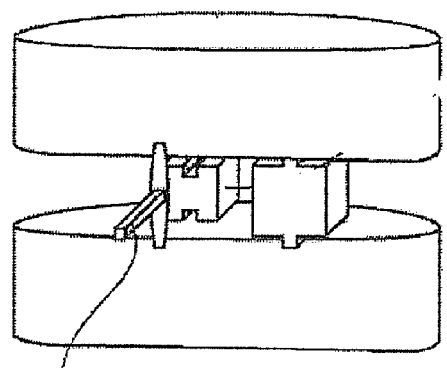

To date, no tool or device has been developed that can provide these features to ensure proper insertion of a multi-assembly artificial disc. As shown in FIGS. 64-65, a trial may be used to accurately form channels or grooves at a predetermined distance. Turning to FIG. 64, a trial may be used to cut upper and/or lower channels in facing endplates of two vertebral bodies. Additionally, the trial may smooth portions of the endplate surfaces where an assembly may travel or ultimately be disposed. The trial may be inserted in a direction that corresponds to the path that will be used to insert the assembly. As mentioned above, the insertion path of the assembly may not always correspond to anterior-posterior axis of the vertebral bodies. For instance, an angle formed between the direction of the insertion path for the assemblies and the anterior-posterior axis may be from about 20° to about 70°, or may be from about 30° to about 60°. The path also may form a circular arc having a radius of curvature corresponding to the curvature of the ridges or keels of the plates. In this manner, the assembly may be rotated or turned into its final position as it moves along the channels or grooves.

Once the trial has formed this first channel and groove or plurality of channels and grooves, a guide may be used to determine where a second set of channels or grooves may be formed. In general, the guide is in communication with and extends from the first trial. As shown in FIG. 65, the guide may be disposed within a central portion of the trial. Once the trial is in its proper position, the guide may then be deployed a predetermined distance. A portion of the free end of the guide may have a configuration that can receive a second cutting tool. The second cutting tool may then be used to form a second plurality of grooves or channels and to otherwise prepare a second region of the treated area to receive a second assembly. The guide and trial may then be removed and the assemblies inserted into the treated area.

The plates used to contact with the endplates of the upper or lower vertebral bodies of the treated area should have sufficient size to distribute loading over an area of the vertebral body to prevent failure of the endplates. Thus, one or more of the rigid plates may have a length from about 25 to about 32 mm, and more preferably from about 28 to about 30 mm. Likewise, the width of one or more plates may be from about 10 to about 18 mm, and more preferably is about 12 to abut 14 mm.

Figure 68:
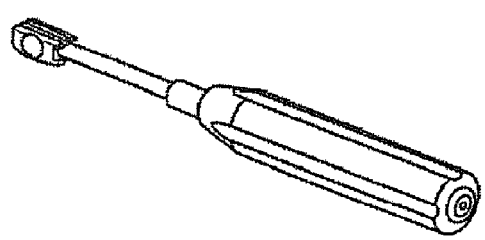

In another embodiment illustrated in FIG. 68, a trial may be capable of connecting with a handle having a detachable grip. In one embodiment, the trial may have a chisel guide and keyed recess. This tool, among others may be used to facilitate installation of one or more disc assemblies from a posterior approach in the following exemplary manner.

Figure 70:
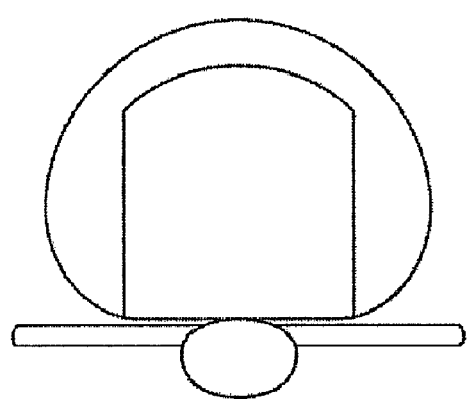

As shown in FIG. 70, a physician may first perform a discectomy in the treated area. In one embodiment, the discectomy is performed so that a perimeter region of the annulus is not removed. For instance, a 1 mm to 7 mm, and more preferably 3 mm to 5 mm, wide region along the perimeter of the anterior side of the vertebral body may remain after the discectomy is completed.

When viewed from the posterior side, the spinal cord may obstruct the view of a central portion of the vertebral bodies thereby leaving two posterior sides of the vertebral body for inserting disc assemblies. If desired, a distractor may be used on the contra-lateral side while a trial is inserted on the other side. When a posterior approach is used, a preferred embodiment of the invention is to use 2 disc assemblies where one is placed in the treated area from one side of the spinal cord and the other is inserted from the other side.

In another embodiment, the trial itself may be used to distract the vertebral bodies. The physician may assess the treated area and select a suitable disc a suitable disc assembly from a plurality provided in a kit. Factors that may be considered when selecting a disc assembly may include, among others, the footprint of the disc assembly, lordosis, disc assembly height, and isze.

As shown in FIG. 62C, if one or more sliding surfaces of the prosthetic disc is substantially spherical in curvature, it is desirable to position the disc assemblies a predetermined distance apart from each other and in proper alignment to allow portions of the 2 disc assemblies that form the sliding surface to cooperate. Providing a keel on each disc assembly may be useful for properly separating (if needed) and aligning each assembly with respect to each other and possibly also with respect to the treated area. For instance, 2 disc assemblies may be configured such that a keel on one assembly should be approximately 13 mm from the center of a keel on the second disc assembly. The distance between keels may be varied to account for differences in the radius of curvature of the sliding surfaces, the location of the keel on each disc assembly, the condition of the anatomy in the treated area, and the like.

While the precise distance between keels does not need to be specified, the physician should understand how to align and position the disc assemblies. For instance, the distance between keels for proper alignment may be selected from a range from about 5 mm to about 20 mm, or from about 10 mm to about 15 mm, and the selected distance may then be provided to the physician or accounted for in the tools provided to the physician.

Figure 71:
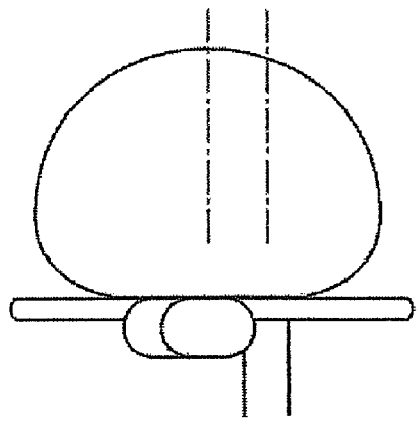

In one embodiment, each of the two disc assemblies is positioned and aligned a predetermined distance from the midline of the vertebral body in the anterior-posterior direction. For instance, as shown in FIG. 71, the trial may be inserted into the treated area on one side of the spinal cord such that the center of the chisel guide, when properly positioned, is from about 3 mm to about 10 mm from the midline of the vertebral body. More preferably, the center of the chisel guide when properly positioned is from about 4 mm to about 8 mm from the midline of the vertebral body.

Once the trial is in its proper position, the grip of the handle may be removed. Preferably, the handle is formed of at least a detachable grip and a shaft in communication with the trial. When the grip is removed, the shaft may then be used as a guide rod for additional tooling and instruments.

For example, once the grip is removed, the shaft may be used as a guide for applying a chisel to form grooves or channels in the treated area. More specifically, with reference to FIGS. 72 and 73, a chisel may be provided that can slidingly engage with the shaft of the handle to help ensure that the chisel is positioned properly for forming a channel or groove in one or both vertebral bodies adjacent to the treated area. In one embodiment, a portion of the chisel forms a tube or aperture having a cross-section corresponding approximately in the cross-section of the handle shaft. The tube or aperture may be slightly larger to allow for the chisel to move more easily along the length of the shaft.

Figure 72:
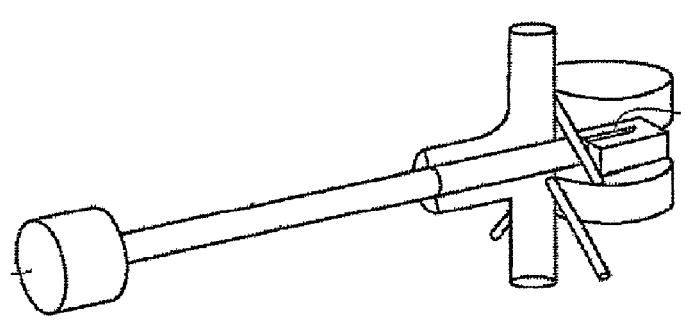
Figure 73:
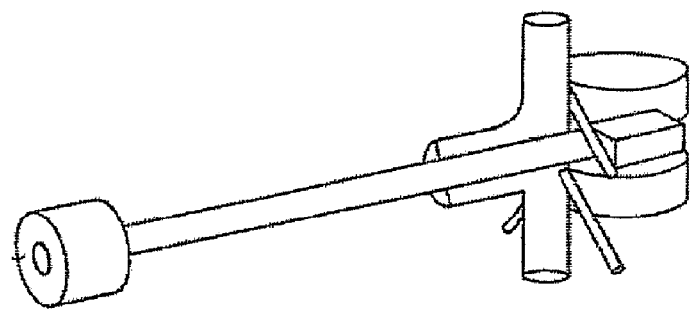

As shown in FIG. 72, the end of the chisel that impacts against, cuts, or otherwise contacts the vertebral bodies has chisel blades that may be shaped and configured to form grooves or channels in the vertebral bodies of a desired shape. Thus, in our embodiment, the cross-sectioned shape of the chisel blade is a truncated wedge. In one embodiment, the cross-section of the chisel blade may be approximately the same as the cross-section of the keel of the disc assembly. The end of the chisel opposite the chisel blade may have an enlarged impaction face. Thus, the physician may align and position the chisel blades against one or more vertebral bodies neighboring the treated area and strike the impaction face to drive the blades into the vertebral bodies. As the chisel blades are worked into the treated area, the blades may be guided and maintained in proper position by slidingly engaging with the chisel guide formed on the trial. Preferably, the length of the chisel may be selected such that the chisel blades have progressed to their desired position when the impaction face is flush with the handle shaft.

Figure 74:
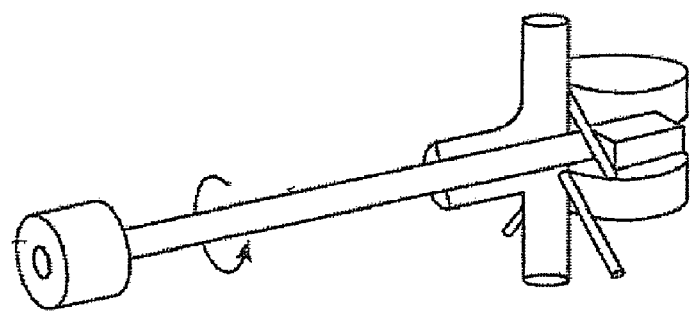
Figure 75:
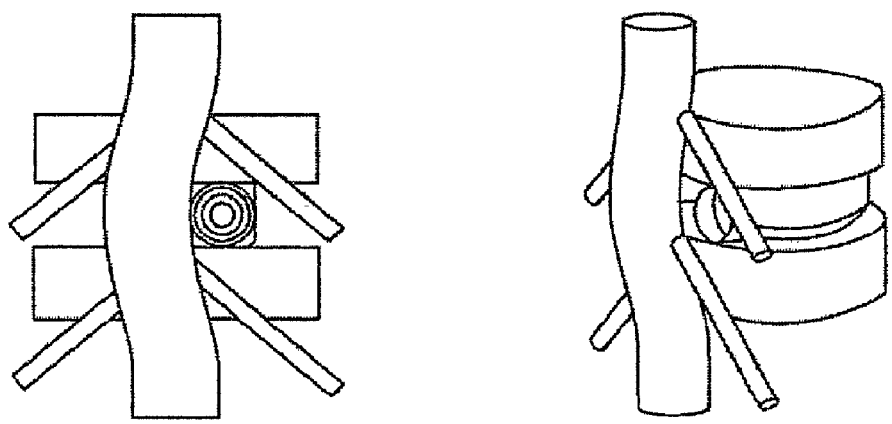

In one embodiment the chisel blade may be selectively detached from the chisel. As shown in FIG. 74, for example, the impaction face and chisel tube may be separated from the chisel blades and removed. Likewise, the trial may be selectively detached from the handle shaft. Thus it is possible to remove these components of the instruments and leave the trial and chisel blade in the treated area, as shown in FIG. 75.

Turning to FIG. 76, with the trial and chisel blades remaining in position, the spinal cord may be repositioned or moved slightly to provide access to the contra-lateral side of the treated area. As previously discussed, the trial may be configured with a keyed recess. The keyed recess is positioned so that it faces toward the contra-lateral side of the treated area (i.e., toward the midline of the vertebral body in the A-P direction). Alternatively, the trial may be configured with two keyed recesses formed on opposing lateral faces of the trial. This configuration would permit the trial to be inserted on either side of the spinal cord. As shown in FIG. 77A, an angled guide may then be inserted into the treated area on the contra-lateral side of the area from the trial and chisel blade. The angled guide may be selectively engaged with a keyed recess of the trial. Once the angled guide is in communication or proper registration with the keyed recess, the shaft extending outward of the treated area may then be used to insert a second chisel blade into the treated area. As shown in FIG. 77B, the cross section of the shaft of the angled guide may be oval, rectangular, square, triangular, oblong, elliptical, or have some other shape that helps prevent rotation of a chisel blade as it is being inserted. Of course, it is preferable that the chisel blade has a tube or aperture corresponding generally to the shape of the cross-section of the angled guide. Preferably, the second chisel is substantially the same size as the first. The blade may then be placed on the shaft of the angled guide and positioned near or adjacent to the vertebral bodies. A chisel tube and impaction face may once again be employed to drive the chisel blade into the treated area.

Once the chisel blade has been fully displaced in the contra-lateral side, it may then be removed from the treated area along with the angled guide. In one embodiment, both the chisel blade and angled guide are removed at the same time (i.e., the angled guide may be removed with the chisel blade still disposed on the shaft). As shown in FIG. 78, a disc assembly may then be deployed into the contra-lateral side. To facilitate insertion of the disc assembly, an implant holder may be used to securely grip the assembly until its keels are inserted into the grooves or channels formed by the chisel. FIG. 78 illustrates one embodiment where the implant holder may selectively engage with the rear-most or posterior side of the disc assembly. Configuring the disc assembly and implant holder in this manner allows the overall height and width needed for insertion of the disc assembly to remain at a minimum.

Alternatively, the implant holder may engage with the outermost upper and lower surfaces of the disc assembly, on either side of the keels. However, this configuration may require the vertebral bodies to be distracted during insertion, thereby potentially causing the first chisel blade and/or the trial to become dislodged from their positions. Additionally, an implant holder may grip the disc assembly from the lateral sides, however, this too may require an increase in the overall size of the window or opening needed in order to insert the disc assembly. Thus, while these alternative embodiments may be used and may fall within the scope of the invention, there may be disadvantages to them.

Once the keels of the disc assembly have begun to be positioned on over th channels or grooves, the implant holder may be used to push the disc assembly into the treated area. As the disc assembly nears its final position, resistance between the vertebral bodies and the surfaces of the disc assembly may significantly resist further progress. If desired or needed, gentle impact forces may be applied to the implant holder to aid in moving the disc assembly into position.

The first chisel blade and trial may then be removed and a second disc assembly inserted in a similar manner. In particular, the chisel blade may be operatively connected with the chisel tube or another instrument and then withdrawn from the body. Likewise, the handle shaft, and optionally the grip, may be reconnected to the trial so that it too can be withdrawn. The removal of the trial and chisel blade can be performed at the same time or sequentially. Once the trial and chisel blades have been removed, the second disc assembly may be inserted. FIG. 79 illustrates one embodiment where two disc assemblies have been inserted from a posterior approach into their desired positions.

Figure 80:
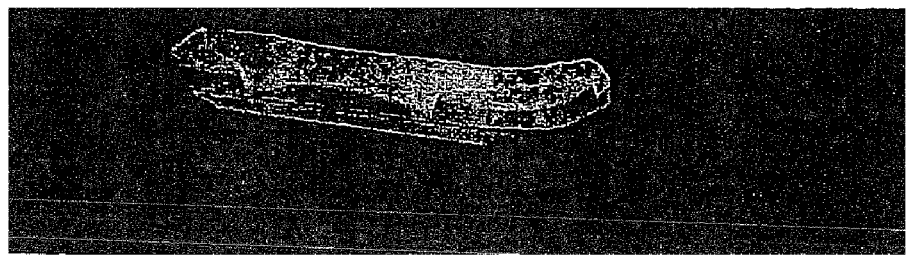
Figure 81:
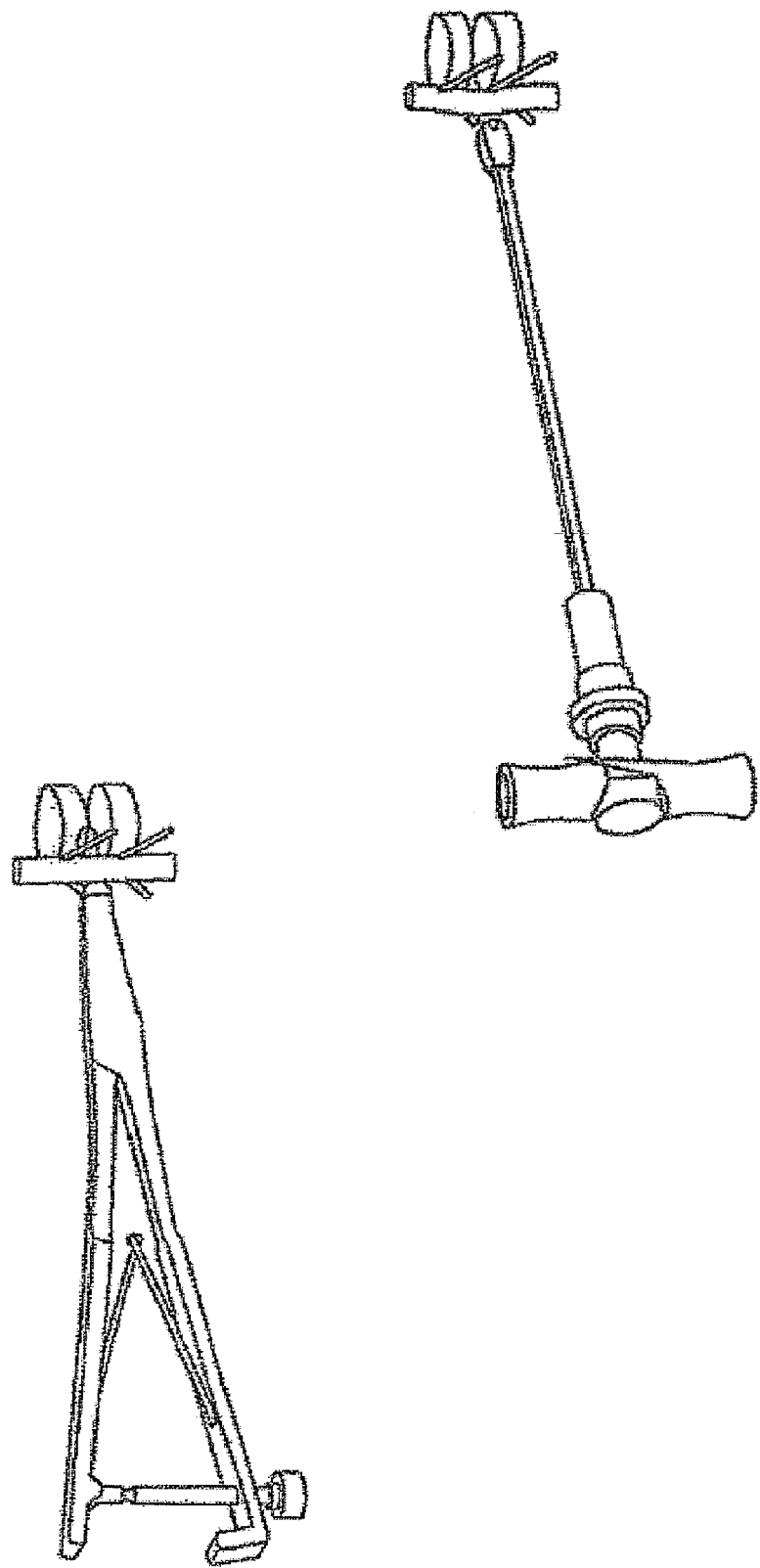

As mentioned previously, the keel of a disc assembly may be configured to promote or permit bony ingrowth that may help hold the disc assembly in place more securely. FIG. 80 illustrates one embodiment of a keel having a plurality of slots or cuts formed in it. The slots or cuts may extend at an angle, such as from about 5° to about 40° off from a vertical direction, and more preferably from about 10° to about 30°. A keel may have two or more, or even three or more slots or cuts. One skilled in the art would appreciate that other configurations may also be used to promote bony ingrowth that might help further secure the disc assembly in place. For instance, the keel may have holes or apertures drilled into it, longitudinal slots may be formed, and the sidewalls of the keel may be textured with one or more grooves or channels that does not extend fully through the keel to the opposing sidewall.

In addition, the face of the keel that first inserted into a groove or channel may have a taper or chamfer. One potential advantage of configuring a keel with a taper or chamfer on its face is that it may assist in aligning the keel with the opening of the channel or groove. Also, a chamfered or tapered face may help reduce drag forces and undesired cutting or gouging of the channel or groove as the keel is pushed toward its final position.

One advantage of providing multiple assemblies to form the artificial disc is that it allows the assemblies to be placed into position without significant vessel retraction. Thus, insertion from the anterior of the vertebral bodies can be achieved with minimal repositioning of the vena cava or aorta. Because the wall of the vena cava is a thin, it punctures or tears more readily than other vessels.

Conversely, the wall of the aorta is thicker than the vena cava, and therefore more resistant to tearing or punctures, but the pressure of the blood supply is considerably higher. As a result, damage to the aorta can result in significant blood loss. Therefore, one benefit of a multi-assembly artificial disc is the reduced need to disturb or move these major blood vessels.

Another advantage to using a multi-assembly configuration is that it permits a physician to adjust or replace one or more assemblies from a different approach than used during the original insertion of the disc. When an implant is placed in a region of the spine, a region surrounding the area of insertion can become obscured or blocked by scar tissue that gradually forms after the procedure. This scar tissue can also bind to neighboring anatomy, including the major blood vessels so that it is extremely difficult to reuse the insertion window again without substantial risk to the patient.

When multiple assemblies are used, however, it is possible to use a second approach to adjust, remove, or replace the artificial disc. For instance, if disc assemblies are inserted into position from the anterior side of the vertebral body, it would be possible to remove or adjust the assemblies using a posterior approach using the methods, tools, and techniques described herein. Likewise, a multi-assembly artificial disc can be inserted from a posterior direction, thereby leaving the anterior side available for future access to the disc.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

We claim:

1. An intervertebral artificial disc for replacement of a damaged spinal disc between two vertebrae having facing endplates comprising:

a first rigid plate having a first surface configured and adapted to substantially engage with a first endplate of a first vertebral body, wherein said first rigid plate comprises a contoured, partially spherical seating surface;

a second rigid plate having a second surface configured and adapted to engage with a second endplate of a second vertebral body, wherein said second rigid plate comprises a contoured, partially cylindrical seating surface;

first core elements at least partially disposed between the first and second rigid plates, wherein said first core element comprises a first contoured surface in communication with and substantially corresponding to the curvature of the first rigid plate seating surface, and a second contoured surface substantially in communication with and substantially corresponding to the curvature of the second rigid plate seating surfaces, wherein the contact between the second rigid plate seating surface and the second contoured surface of the first core element forms a line of contact a third rigid plate configured and adapted to engage with the first endplate of the first vertebral body, wherein said third rigid plate comprises a contoured, partially spherical seating surface having substantially the same radius of curvature as the first rigid plate seating surface;

a fourth rigid plate configured and adapted to engage with the second endplate of the second vertebral body, wherein said fourth rigid plate comprises a contoured, partially cylindrical seating surface having substantially the same radius of curvature as the second rigid plate seating surface; and a second core element at least partially disposed between the third and fourth rigid plates, wherein said second core element comprises a first contoured surface substantially corresponding to the curvature of the third rigid plate seating surface, and a fourth contoured surface substantially corresponding to the curvature of the fourth rigid plate seating surface;

wherein said third rigid plate, fourth rigid plate, and second core element form a second assembly wherein the first rigid plate having one portion of the semi-spherical curvature and the third rigid plate having a second portion of the semi-spherical curvature and the first and second portions define a complete spherical curvature wherein the first rigid plate and the third rigid plate are spaced apart to maintain a constant diameter of the spherical curvature of the first and third rigid plates, wherein the second rigid plate comprises a constraining element for retaining the first core element within the contoured cylindrical seating surface;

wherein the fourth rigid plate comprises a constraining element for retaining the second core element within the contoured cylindrical seating surface.

2. The artificial disc of claim 1, wherein the first surface of the first rigid plate is configured to correspond to the natural curvature and shape of the first endplate of the first vertebral body.

3. The artificial disc of claim 2, wherein the second surface of the second rigid plate is configured to correspond to the natural curvature and shape of the second endplate of the second vertebral body.

4. The artificial disc of claim 1, wherein the first surface of the first rigid plate or the second surface of the second rigid plate is configured to correspond to a predetermined cut shape or contour.

5. The artificial disc of claim 4, wherein the first or second surface is substantially flat.

6. The artificial disc of claim 1, wherein the second rigid plate seating surface and the core element second contoured surface permit rotation of the core element relative to the second rigid plate substantially in the sagittal plane.

7. The artificial disc of claim 6, wherein the second rigid plate has a longitudinal axis and wherein the axis of rotation of the core element forms an angle from about 20° to about 70°.

8. The artificial disc of claim 7, wherein the angle between the second rigid plate longitudinal axis and the core element axis of rotation forms an angle from about 30° to about 60°.

9. The artificial disc of claim 7, wherein the second rigid plate has a longitudinal axis and wherein the axis of rotation of the core element is substantially perpendicular to the longitudinal axis.

10. The artificial disc of claim 6, wherein the second rigid plate has a longitudinal axis and wherein the axis of rotation of the core element is substantially parallel to the longitudinal axis.

11. The artificial disc of claim 6, wherein the artificial disk is capable of providing a moving JAR in the sagittal plane.

12. The artificial disc of claim 1, wherein contact between the first rigid plate seating surface and the first contoured surface of the first core element extends over an area.

13. The artificial disc of claim 12, wherein the contact between the second rigid plate seating surface and the second contoured surface of the first core element extends over an area.

14. The artificial disc of claim 1, wherein the contact between the second rigid plate seating surface and the second contoured surface of the first core element extends over an area.

15. The artificial disc of claim 1, wherein the first rigid plate is disposed above the first core element and the second rigid plate is disposed below the first core element.

16. The artificial disc of claim 1, wherein the first rigid plate comprises a first raised ridge of material that extends at least partially into the first endplate of the first vertebral body.

17. The artificial disc of claim 16, wherein the second rigid plate comprises a second raised ridge of material that extends at least partially into the second endplate of the second vertebral body.

18. The artificial disc of claim 1, wherein the first core element is at least partially formed of an elastomeric material.

19. The artificial disc of claim 1, further comprising mechanical stops that prevent lateral bending greater than 10 degrees in each direction.

20. The artificial disc of claim 1, further comprising mechanical stops that prevent total axial rotation greater than 5 degrees.

21. The artificial disc of claim 1, wherein the curvature of the second rigid plate seating surface is convex.

22. The artificial disc of claim 1, wherein the curvature of the second rigid plate seating surface is concave.

23. The artificial disc of claim 1, wherein the first rigid plate has a length from about 18 to about 35 mm.

24. The artificial disc of claim 23, wherein the first rigid plate has a length from about 22 to about 26 mm.

25. The artificial disc of claim 23, wherein the first rigid plate has a width from about 9 mm to about 18 mm.

26. The artificial disc of claim 25, wherein the first rigid plate has a width from about 12 to about 14 mm.

27. The artificial disc of claim 1, wherein the first rigid plate has a width from about 7 mm to about 15 mm.

28. The artificial disc of claim 27, wherein the first rigid plate has a width from about 8 to about 12 mm.

29. The artificial disc of claim 1, wherein the first rigid plate has a width from about 12 mm to about 36 mm.

30. The artificial disc of claim 29, wherein the first rigid plate has a width from about 16 mm to about 28 mm.

31. The artificial disc of claim 1, wherein the core element and first rigid plate are formed from substantially similar materials.

32. The artificial disc of claim 31, wherein the core comprises a high molecular weight polymeric material.

33. The artificial disc of claim 32, wherein the core comprises a high molecular weight polyethylene.

34. The artificial disc of claim 32, wherein the core further comprises a radio opaque marker that is capable of indicating the orientation of the core.

35. The artificial disc of claim 34, wherein the radio opaque marker comprises two metallic pins.

36. The artificial disc of claim 1, wherein the core element is formed from a different material that the first rigid plate.

37. A method for replacing a damaged spinal disc between two vertebrae having facing endplates with an artificial disc comprising the steps of:

removing a damaged spinal disc disposed between a first vertebral body and a second vertebral body;

providing a first artificial disc assembly comprising:

a first rigid plate configured and adapted to engage with a first endplate of the first vertebral body, wherein said first rigid plate comprises a contoured, partially spherical seating surface;

a second rigid plate configured and adapted to engage with a second endplate of the second vertebral body, wherein said second rigid plate comprises a contoured, partially cylindrical seating surface; and a first core element at least partially disposed between the first and second rigid plates, wherein said first core element comprises a first contoured surface in communication with and substantially corresponding to the curvature of the first rigid plate seating surface, and a second contoured surface substantially in communication with and substantially corresponding to the curvature of the second rigid plate seating surface;

a third rigid plate configured and adapted to engage with the first endplate of the first vertebral body, wherein said third rigid plate comprises a contoured, partially spherical seating surface having substantially the same radius of curvature as the first rigid plate seating surface;

a fourth rigid plate configured and adapted to engage with the second endplate of the second vertebral body, wherein said fourth rigid plate comprises a contoured, partially cylindrical seating surface having substantially the same radius of curvature as the second rigid plate seating surface; and a second core element at least partially disposed between the third and fourth rigid plates, wherein said second core element comprises a first contoured surface substantially corresponding to the curvature of the third rigid plate seating surface, and a fourth contoured surface substantially corresponding to the curvature of the fourth rigid plate seating surface;

wherein said third rigid plate, fourth rigid plate, and second core element form a second assembly wherein the first rigid plate having one portion of the semi-spherical curvature and the third rigid plate having a second portion of the semi-spherical curvature and the first and second portions define a, complete spherical curvature, wherein the first rigid plate and the third rigid plate are spaced apart to maintain a constant diameter of the spherical curvature of the first and third rigid plates, wherein the second rigid plate comprises a constraining element for retaining the first core element within the contoured cylindrical seating surface;

wherein the fourth rigid plate comprises a constraining element for retaining the second core element within the contoured cylindrical seating surface removing at least a portion of a posterior element of the spine, preparing the first endplate and second endplate for receiving the artificial disc assembly;

positioning the first artificial disc assembly between the first and second vertebral bodies such that the first rigid plate at least partially engages with the first endplate of the first vertebral body and the second rigid plate at least partially engages with the second endplate of the second vertebral body.

38. The method of claim 37, wherein the first disc assembly and the second disc assembly cooperate to provide bending, rotation, and translation of the first vertebral body relative to the second vertebral body.

39. The method of claim 37, wherein the step of preparing the first endplate and second endplate for receiving the artificial disc assembly comprises the steps of:

providing a trial comprising:

a first protrusion on its superior surface that is capable of cutting a portion of the first endplate; and a second protrusion on its inferior surface that is capable of cutting a portion of the second endplate;

cutting a portion of the first endplate where the first rigid plate will be received;

cutting a portion of the second endplate where the second rigid plate will he received;

extending a guide a predetermined distance from one side of the trial toward a location where the second assembly will be disposed;

providing a cutting tool in communication with the guide;

cutting a portion of the first endplate where the third rigid plate will be received; and cutting a portion of the second endplate where the fourth rigid plate will be received.

40. The method of claim 37, further comprising the step of removing at least a portion of a posterior facet of the spine.

41. The method of claim 40, wherein the step of removing at least a portion of the transverse process preserves the structure of the vertebral foramen.

42. The method of claim 40, further comprising providing an insertion path for the first assembly, wherein the first vertebral body has an anterior-posterior axis, and wherein an angle formed between the direction of the insertion path for the assemblies and the anterior-posterior axis is from about 20° to about 70°.

43. The method of claim 42, wherein the angle formed between the insertion path and anterior-posterior axis is from about 30° to about 60°.

44. An intervertebral artificial disc for replacement of a damaged spinal disc between two vertebrae having facing endplates comprising:

a first rigid plate having a first surface configured and adapted to substantially engage with a first endplate of a first vertebral body, wherein said first rigid plate comprises a contoured, partially spherical seating surface;

a second rigid plate having a second surface configured and adapted to engage with a second endplate of a second vertebral body, wherein said second rigid plate comprises a contoured, partially spherical seating surface;

a first core element at least partially disposed between the first and second rigid plates, wherein said first core element comprises a first contoured surface in communication with and substantially corresponding to the curvature of the first rigid plate seating surface, and a second contoured surface substantially in communication with and substantially corresponding to the curvature of the second rigid plate seating surface;

a third rigid plate configured and adapted to engage with the first endplate of the first vertebral body, wherein said third rigid plate comprises a contoured, partially spherical seating surface having substantially the same radius of curvature as the first rigid plate seating surface;

a fourth rigid plate configured and adapted to engage with the second endplate of the second vertebral body, wherein said fourth rigid plate comprises a contoured, partially cylindrical seating surface having substantially the same radius of curvature as the second rigid plate seating surface; and a second core element at least partially disposed between the third and fourth rigid plates, wherein said second core element comprises a first contoured surface substantially corresponding to the curvature of the third rigid plate seating surface, and a fourth contoured surface substantially corresponding to the curvature of the fourth rigid plate seating surface;

wherein said third rigid plate, fourth rigid plate, and second core element form a second assembly wherein the first rigid plate having one portion of the semi-spherical curvature and the third rigid plate having a second portion of the semi-spherical curvature and the first and second portions define a complete spherical curvature, wherein the first rigid plate and the third rigid plate are spaced apart such that the spherical curvature of the first and third rigid plates are maintained at a constant diameter, wherein the second rigid plate comprises a constraining element for retaining the first core element within the contoured cylindrical seating surface;

wherein the fourth rigid plate comprises a constraining element for retaining the second core element within the contoured cylindrical seating surface;

wherein the contact between the second rigid plate seating surface and the second contoured surface of the first core element forms a line of contact wherein the intervertebral artificial disc is capable providing of a moving instantaneous axis of rotation substantially in the sagittal plane.

45. The artificial disc of claim 44, further comprising a stop extending from the seating surface of the first rigid plate toward a channel formed in the core.

46. The artificial disc of claim 44, further comprising a stop extending from the seating surface of the second rigid plate toward a channel formed in the core.

47. The artificial disc of claim 44, further comprising a stop extending from the first or second seating surface toward a channel formed in the core, wherein the channel and stop cooperate to limit the range of motion of the core relative to one of the rigid plates.

48. The artificial disc of claim 47, wherein the channel and stop cooperate to limit motion of the core relative to one rigid plate substantially to the sagittal plane.

49. The artificial disc of claim 48, wherein the channel and stop are capable of preventing the core from being inadvertently expelled from between the first and second rigid plates.

* * * * *